United States Patent
Tian et al.

(10) Patent No.: US 10,806,769 B2
(45) Date of Patent: Oct. 20, 2020

(54) ANTIMICROBIAL PEPTIDE STIMULATING CLEANSING COMPOSITION

(71) Applicant: GOJO Industries, Inc., Akron, OH (US)

(72) Inventors: Kegui Tian, Hudson, OH (US); Jessica Rae Tittl, Chagrin Falls, OH (US); Venkatesan V. Padyachi, Kendall Park, NJ (US)

(73) Assignee: GOJO Industries, Inc., Akron, OH (US)

( * ) Notice: Subject to any disclaimer, the term of this patent is extended or adjusted under 35 U.S.C. 154(b) by 0 days.

(21) Appl. No.: 15/476,018

(22) Filed: Mar. 31, 2017

(65) Prior Publication Data

US 2017/0281717 A1 Oct. 5, 2017

Related U.S. Application Data

(60) Provisional application No. 62/316,123, filed on Mar. 31, 2016.

(51) Int. Cl.
| | |
|---|---|
| *A61K 36/00* | (2006.01) |
| *A61K 38/08* | (2019.01) |
| *A61K 8/64* | (2006.01) |
| *A61Q 17/00* | (2006.01) |
| *A61K 8/97* | (2017.01) |
| *A61K 9/00* | (2006.01) |
| *A61K 36/55* | (2006.01) |
| *A61K 38/07* | (2006.01) |
| *A61K 47/20* | (2006.01) |
| *A61L 2/00* | (2006.01) |

(52) U.S. Cl.
CPC .......... *A61K 38/08* (2013.01); *A61K 8/64* (2013.01); *A61K 8/97* (2013.01); *A61K 9/0014* (2013.01); *A61K 36/55* (2013.01); *A61K 38/07* (2013.01); *A61K 47/20* (2013.01); *A61L 2/0088* (2013.01); *A61Q 17/005* (2013.01); *A61K 2800/596* (2013.01); *A61L 2202/20* (2013.01)

(58) Field of Classification Search
CPC .................................................. A61K 36/00
See application file for complete search history.

(56) References Cited

U.S. PATENT DOCUMENTS

| | | |
|---|---|---|
| 5,269,959 A | 12/1993 | Schreibman |
| 5,352,437 A | 10/1994 | Nakagawa et al. |
| 5,453,121 A | 9/1995 | Nicholls et al. |
| 5,942,479 A | 8/1999 | Frankenbach et al. |
| 5,952,278 A | 9/1999 | Mao et al. |
| 5,981,473 A | 11/1999 | Barefoot |
| 6,040,154 A | 3/2000 | Fayolle et al. |
| 6,210,656 B1 * | 4/2001 | Touzan ............... A61K 8/046 424/45 |
| 6,221,847 B1 | 4/2001 | Barefoot |
| 6,235,272 B1 | 5/2001 | Greene |
| 6,358,516 B1 | 3/2002 | Harod |
| 6,376,438 B1 * | 4/2002 | Rosenberger ............ A61K 8/39 510/138 |
| 6,423,329 B1 | 7/2002 | Sine et al. |
| 6,509,021 B1 | 1/2003 | Weiss et al. |
| 6,673,755 B2 | 1/2004 | Wei et al. |
| 6,733,751 B2 | 5/2004 | Farmer |
| 6,760,331 B1 | 5/2004 | Stoll |
| 6,797,683 B2 | 9/2004 | Shana'a et al. |
| 6,814,958 B1 | 11/2004 | Sekimoto |
| 6,849,256 B1 | 2/2005 | Farmer |
| 6,905,673 B2 | 6/2005 | Rajaiah et al. |
| 6,924,256 B2 | 8/2005 | Massaro et al. |
| 7,025,955 B2 | 4/2006 | Siddiqui et al. |
| 7,070,814 B2 | 7/2006 | Qazi et al. |
| 7,198,780 B2 | 4/2007 | Dicianna |
| 7,241,452 B2 | 7/2007 | Veeger et al. |
| 7,429,292 B2 | 9/2008 | McIntosh et al. |
| 7,452,545 B2 | 11/2008 | Yu |
| 7,494,661 B2 | 2/2009 | Sanders |
| 7,507,402 B1 | 3/2009 | Farmer et al. |
| 7,510,734 B2 | 3/2009 | Sullivan et al. |
| 7,514,105 B2 | 4/2009 | Qazi et al. |
| 7,517,852 B2 | 4/2009 | Walsh et al. |
| 7,541,042 B2 | 6/2009 | Farmer |
| 7,547,527 B2 | 6/2009 | Baur |

(Continued)

FOREIGN PATENT DOCUMENTS

| | | |
|---|---|---|
| BR | PI 201010487 | 10/2013 |
| CN | 101129311 A * | 2/2008 |

(Continued)

OTHER PUBLICATIONS

International Search Report and Written Opinion from PCT/US2017/025326 dated Jun. 9, 2017.
International Search Report and Written Opinion from PCT/US2017/025319 dated Jul. 17, 2017.
International Search Report and Written Opinion from PCT/US2017/025324 dated Jun. 14, 2017.
International Search Report and Written Opinion from PCT/US2017/025323 dated Jun. 27, 2017.
Firas A Al-Bayati, "Antibacterial Activity of Linum Usitati Ssimum L. Seeds and Active Compound Detection", Rafi Dai N Journal of Science, Mosul University Faculty, IQ, vol. 18, No. 2, Jan. 1, 2007, pp. 27-36.

(Continued)

*Primary Examiner* — Qiuwen Mi
(74) *Attorney, Agent, or Firm* — Calfee, Halter & Griswold LLP

(57) ABSTRACT

A topical cleansing composition for stimulating the production of antimicrobial peptides on the skin is disclosed. The topical cleansing composition includes an active ingredient comprising one or more of a natural extract and a polypeptide; one or more surfactants; and water. The topical cleansing composition increases the concentration of antimicrobial peptides on skin, as compared to an otherwise identical topical composition without the active ingredient.

11 Claims, 11 Drawing Sheets

(56) References Cited

U.S. PATENT DOCUMENTS

| | | |
|---|---|---|
| 7,560,125 B2 | 7/2009 | Ananthapadmanabhan et al. |
| 7,611,882 B2 | 11/2009 | Bjornvad et al. |
| 7,612,027 B2 | 11/2009 | Grasha et al. |
| 7,618,801 B2 | 11/2009 | Jones et al. |
| 7,632,527 B2 | 12/2009 | Jochim et al. |
| 7,651,680 B2 | 1/2010 | Breton et al. |
| 7,666,824 B2 | 2/2010 | Krzysik et al. |
| 7,713,726 B2 | 5/2010 | Farmer |
| 7,758,878 B2 | 7/2010 | Scimeca et al. |
| 7,776,346 B2 | 8/2010 | O'Connor et al. |
| 7,803,746 B2 | 9/2010 | Luu et al. |
| 7,820,420 B2 | 10/2010 | Whitlock |
| 7,824,665 B2 | 11/2010 | Miyamoto et al. |
| 7,910,143 B2 | 3/2011 | Kvist et al. |
| 7,928,087 B2 | 4/2011 | Fack et al. |
| 7,939,107 B2 | 5/2011 | Pleva |
| 8,034,385 B2 | 10/2011 | Golz-Berner et al. |
| 8,067,351 B2 | 11/2011 | Holerca et al. |
| 8,080,258 B2 | 12/2011 | Rothman |
| 8,084,409 B2 | 12/2011 | Lucka et al. |
| 8,088,174 B2 | 1/2012 | Neplaz et al. |
| 8,097,573 B2 | 1/2012 | Lutrario et al. |
| 8,101,214 B2 | 1/2012 | Park et al. |
| 8,114,658 B2 | 2/2012 | Muroyama et al. |
| 8,119,583 B2 | 2/2012 | Day et al. |
| 8,124,573 B2 | 2/2012 | Focht et al. |
| 8,137,706 B2 | 3/2012 | Al-Ghazzewi et al. |
| 8,173,143 B2 | 5/2012 | Tecco |
| 8,222,020 B2 | 7/2012 | Brusk et al. |
| 8,236,744 B2 | 8/2012 | Boyke et al. |
| 8,246,946 B2 | 8/2012 | Cobb et al. |
| 8,257,753 B2 | 9/2012 | Dal Farra et al. |
| 8,283,136 B2 | 10/2012 | Tagg et al. |
| 8,318,659 B2 | 11/2012 | Lowe et al. |
| 8,329,672 B2 | 12/2012 | Prous et al. |
| 8,333,954 B2 | 12/2012 | Seidling et al. |
| 8,337,915 B2 | 12/2012 | Aburdeineh |
| 8,349,803 B2 | 1/2013 | Dal Farra et al. |
| 8,361,450 B2 | 1/2013 | Johnson et al. |
| 8,377,679 B2 | 2/2013 | Baur et al. |
| 8,420,627 B2 | 4/2013 | Guthery |
| 8,455,411 B2 | 6/2013 | Kilthau et al. |
| 8,481,299 B2 | 7/2013 | Gueniche |
| 8,506,952 B2 | 8/2013 | Minbiole et al. |
| 8,575,083 B2 | 11/2013 | Bettiol et al. |
| 8,586,067 B2 | 11/2013 | Okamoto et al. |
| 8,697,055 B2 | 4/2014 | Farmer |
| 8,753,654 B2 | 6/2014 | Narula et al. |
| 8,753,861 B2 | 6/2014 | Cascao-Pereira et al. |
| 8,772,222 B2 | 7/2014 | Baker et al. |
| 8,778,863 B2 | 7/2014 | Pipko |
| 8,785,171 B2 | 7/2014 | Souter et al. |
| 8,801,864 B2 | 8/2014 | Brooke |
| 8,815,538 B2 | 8/2014 | Lanzalaco et al. |
| 8,821,854 B2 | 9/2014 | Farmer et al. |
| 8,822,179 B2 | 9/2014 | Preston, III et al. |
| 8,834,855 B2 * | 9/2014 | Johnsen ............... A61K 8/33 424/59 |
| 8,859,627 B2 | 10/2014 | Found |
| 8,877,259 B2 | 11/2014 | Florence et al. |
| 8,951,775 B2 | 2/2015 | Castiel et al. |
| 8,956,624 B2 | 2/2015 | Schnittger et al. |
| 8,993,006 B2 | 3/2015 | Hines et al. |
| 8,999,399 B2 | 4/2015 | Lisowsky et al. |
| 9,062,215 B2 | 6/2015 | Cuní Bravo et al. |
| 9,096,821 B1 | 8/2015 | Hope et al. |
| 9,107,920 B2 | 8/2015 | Olsen |
| 9,109,189 B2 | 8/2015 | Perez-Prat Vinuesa et al. |
| 9,125,768 B2 | 9/2015 | Husmark et al. |
| 9,133,417 B2 | 9/2015 | Tajmamet et al. |
| 9,198,852 B2 | 12/2015 | Burt et al. |
| 9,220,736 B2 | 12/2015 | Farmer et al. |
| 9,233,062 B2 | 1/2016 | Florence et al. |
| 9,248,206 B2 | 2/2016 | Brown et al. |
| 9,265,708 B2 | 2/2016 | Yumioka et al. |
| 9,301,982 B2 | 4/2016 | Lefkowitz |
| 2004/0243076 A1 | 12/2004 | Husmark et al. |
| 2005/0137102 A1 * | 6/2005 | Shoaf ............... A61K 8/046 510/138 |
| 2005/0271595 A1 | 12/2005 | Brown |
| 2006/0140899 A1 | 6/2006 | Koenig et al. |
| 2006/0171936 A1 | 8/2006 | Gueniche et al. |
| 2006/0204466 A1 | 9/2006 | Littau et al. |
| 2006/0210499 A1 * | 9/2006 | Hoeffkes ............... A61K 8/22 424/62 |
| 2006/0276369 A1 | 12/2006 | Levecket et al. |
| 2006/0278255 A1 | 12/2006 | Drogue et al. |
| 2007/0020213 A1 | 1/2007 | Tamarkin et al. |
| 2007/0027119 A1 | 2/2007 | Ahmed et al. |
| 2007/0053863 A1 * | 3/2007 | Lee ............... A61Q 19/08 424/74 |
| 2007/0154411 A1 * | 7/2007 | Barth ............... A61K 8/19 424/50 |
| 2008/0045491 A1 | 2/2008 | Fitchmun |
| 2008/0095731 A1 | 4/2008 | Mitra |
| 2008/0107699 A1 | 5/2008 | Spigelman et al. |
| 2008/0112907 A1 | 5/2008 | Chan et al. |
| 2008/0124286 A1 | 5/2008 | Lisson |
| 2008/0139432 A1 | 6/2008 | Peffly et al. |
| 2008/0160043 A1 | 7/2008 | Kim et al. |
| 2008/0193406 A1 | 8/2008 | Rull Prous et al. |
| 2008/0206211 A1 | 8/2008 | Gueniche |
| 2008/0206214 A1 | 8/2008 | Farmer |
| 2008/0226603 A1 | 9/2008 | Al-Ghazzewi et al. |
| 2008/0226756 A1 | 9/2008 | Willemin et al. |
| 2008/0233075 A1 | 9/2008 | Sokolinsky et al. |
| 2008/0233091 A1 | 9/2008 | Ross et al. |
| 2008/0233104 A1 | 9/2008 | Farmer |
| 2008/0241226 A1 | 10/2008 | Abeln et al. |
| 2008/0241263 A1 | 10/2008 | Prous et al. |
| 2008/0247960 A1 | 10/2008 | Yuan |
| 2008/0247993 A1 | 10/2008 | Reindl et al. |
| 2008/0255249 A1 | 10/2008 | Hellwege et al. |
| 2008/0261916 A1 | 10/2008 | Jaszberenyi et al. |
| 2008/0268024 A1 | 10/2008 | Rull Prous et al. |
| 2008/0293669 A1 | 11/2008 | Moriya et al. |
| 2009/0017147 A1 | 1/2009 | Lintner et al. |
| 2009/0022700 A1 | 1/2009 | Cassin et al. |
| 2009/0022819 A1 | 1/2009 | Gueniche et al. |
| 2009/0028805 A1 | 1/2009 | Gueniche et al. |
| 2009/0035294 A1 | 2/2009 | Mahe et al. |
| 2009/0060962 A1 | 3/2009 | Castiel et al. |
| 2009/0068150 A1 | 3/2009 | Park et al. |
| 2009/0068160 A1 | 3/2009 | Castiel et al. |
| 2009/0068161 A1 | 3/2009 | Gueniche et al. |
| 2009/0068219 A1 | 3/2009 | Elie et al. |
| 2009/0074735 A1 | 3/2009 | Joshi |
| 2009/0081143 A1 | 3/2009 | Mammone et al. |
| 2009/0099129 A1 | 4/2009 | Meuser et al. |
| 2009/0123448 A1 | 5/2009 | Bozonnet et al. |
| 2009/0130073 A1 | 5/2009 | Reindl et al. |
| 2009/0136604 A1 | 5/2009 | Breton et al. |
| 2009/0142375 A1 | 6/2009 | Vidal et al. |
| 2009/0143714 A1 | 6/2009 | Millikin et al. |
| 2009/0156563 A1 | 6/2009 | Baschong et al. |
| 2009/0175911 A1 | 7/2009 | Cutting et al. |
| 2009/0180970 A1 | 7/2009 | Tamarkin et al. |
| 2009/0186126 A1 | 7/2009 | Farmer et al. |
| 2009/0202705 A1 | 8/2009 | Meuser et al. |
| 2009/0214497 A1 | 8/2009 | Park et al. |
| 2009/0214501 A1 | 8/2009 | Knapp et al. |
| 2009/0232785 A1 | 9/2009 | Breton et al. |
| 2009/0232892 A1 | 9/2009 | Yamasaki et al. |
| 2009/0232942 A1 | 9/2009 | Degre et al. |
| 2009/0238782 A1 | 9/2009 | Vacher et al. |
| 2009/0252775 A1 | 10/2009 | Arndt et al. |
| 2009/0297482 A1 | 12/2009 | Dicks et al. |
| 2009/0305387 A1 | 12/2009 | Farmer |
| 2009/0317370 A1 | 12/2009 | Lang et al. |
| 2010/0003292 A1 | 1/2010 | Gautier et al. |
| 2010/0021532 A1 | 1/2010 | Rao et al. |
| 2010/0022660 A1 | 1/2010 | Wegner |
| 2010/0030172 A1 | 2/2010 | Husmark et al. |
| 2010/0040710 A1 | 2/2010 | Perrier et al. |

(56) References Cited

U.S. PATENT DOCUMENTS

| | | |
|---|---|---|
| 2010/0055081 A1 | 3/2010 | Richelle et al. |
| 2010/0086520 A1 | 4/2010 | Reindl et al. |
| 2010/0086528 A1 | 4/2010 | Olofsson |
| 2010/0113372 A1 | 5/2010 | Park et al. |
| 2010/0119613 A1 | 5/2010 | Gruber et al. |
| 2010/0120710 A1 | 5/2010 | Watanabe et al. |
| 2010/0121304 A1 | 5/2010 | Zhou et al. |
| 2010/0158988 A1 | 6/2010 | Redmond et al. |
| 2010/0159028 A1 | 6/2010 | Shultz |
| 2010/0190872 A1 | 7/2010 | Sedmak |
| 2010/0196295 A1 | 8/2010 | Alvarado |
| 2010/0197551 A1 | 8/2010 | Bettiol et al. |
| 2010/0197552 A1 | 8/2010 | Koyuncu et al. |
| 2010/0197553 A1 | 8/2010 | Barnabas et al. |
| 2010/0197554 A1 | 8/2010 | Koyuncu et al. |
| 2010/0198177 A1 | 8/2010 | Yahiaoui et al. |
| 2010/0209407 A1 | 8/2010 | Pain et al. |
| 2010/0216892 A1 | 8/2010 | Schmaus |
| 2010/0221226 A1 | 9/2010 | Aubert-Jacquin et al. |
| 2010/0226892 A1 | 9/2010 | Gueniche |
| 2010/0233128 A1 | 9/2010 | Panasenko |
| 2010/0254948 A1 | 10/2010 | Giuliani et al. |
| 2010/0260809 A1 | 10/2010 | Valentova et al. |
| 2010/0272839 A1 | 10/2010 | Gueniche et al. |
| 2010/0278793 A1 | 11/2010 | Gueniche et al. |
| 2010/0291049 A1 | 11/2010 | Izawa et al. |
| 2010/0303931 A1 | 12/2010 | Feltin et al. |
| 2010/0317743 A1 | 12/2010 | Macinga et al. |
| 2010/0330013 A1 | 12/2010 | O'Connell et al. |
| 2010/0330128 A1 | 12/2010 | Kang et al. |
| 2010/0331429 A1 | 12/2010 | Lorant |
| 2011/0002891 A1 | 1/2011 | Minbiole et al. |
| 2011/0027221 A1 | 2/2011 | Fu et al. |
| 2011/0034393 A1 | 2/2011 | Justen et al. |
| 2011/0038840 A1 | 2/2011 | Chen et al. |
| 2011/0052514 A1 | 3/2011 | Justen et al. |
| 2011/0052519 A1 | 3/2011 | Carreno et al. |
| 2011/0064835 A1 | 3/2011 | Martin et al. |
| 2011/0117032 A1 | 5/2011 | Gilding |
| 2011/0143007 A1 | 6/2011 | Stengel |
| 2011/0150952 A1 | 6/2011 | Simonnet et al. |
| 2011/0151009 A1 | 6/2011 | Golz-Berner et al. |
| 2011/0177140 A1 | 7/2011 | Voegeli et al. |
| 2011/0182861 A1 | 7/2011 | Castiel et al. |
| 2011/0182863 A1 | 7/2011 | Jia |
| 2011/0189133 A1 | 8/2011 | Tagg et al. |
| 2011/0189343 A1 | 8/2011 | Hasegawa et al. |
| 2011/0201536 A1 | 8/2011 | O'Connell et al. |
| 2011/0223219 A1 | 9/2011 | Dao et al. |
| 2011/0262558 A1 | 10/2011 | Huckfeldt et al. |
| 2011/0274676 A1 | 11/2011 | Farmer et al. |
| 2011/0280850 A1 | 11/2011 | Starr et al. |
| 2011/0294731 A1 | 12/2011 | Torfi |
| 2011/0301118 A1 | 12/2011 | Koenig |
| 2012/0003178 A1 | 1/2012 | Koenic |
| 2012/0009132 A1 | 1/2012 | Tholath et al. |
| 2012/0027735 A1 | 2/2012 | Beland et al. |
| 2012/0034190 A1 | 2/2012 | Apt et al. |
| 2012/0082657 A1 | 4/2012 | Yim |
| 2012/0107290 A1 | 5/2012 | Prioult et al. |
| 2012/0114776 A1 | 5/2012 | Feher |
| 2012/0121522 A1 | 5/2012 | Gruber et al. |
| 2012/0128755 A1 | 5/2012 | Gruber et al. |
| 2012/0156144 A1 | 6/2012 | Tamarkin et al. |
| 2012/0156171 A1 | 6/2012 | Breton et al. |
| 2012/0164087 A1 | 6/2012 | Carter |
| 2012/0164121 A1 | 6/2012 | Paufique |
| 2012/0165290 A1 | 6/2012 | Dijkhuizen et al. |
| 2012/0178731 A1 | 7/2012 | Guthery |
| 2012/0184626 A1 | 7/2012 | Guerra-Vega |
| 2012/0225029 A1 | 9/2012 | Al-Qahtani |
| 2012/0225035 A1 | 9/2012 | Suchanek et al. |
| 2012/0237494 A1 | 9/2012 | Daly et al. |
| 2012/0251512 A1 | 10/2012 | Farmer et al. |
| 2012/0251625 A1 | 10/2012 | Tasiemski et al. |
| 2012/0258126 A1 | 10/2012 | Scholler et al. |
| 2012/0258152 A1 | 10/2012 | De Heinrich et al. |
| 2012/0263758 A1 | 10/2012 | Chinachoti et al. |
| 2012/0294841 A1 | 11/2012 | Gueniche et al. |
| 2012/0301452 A1 | 11/2012 | Gueniche et al. |
| 2012/0322758 A1 | 12/2012 | Kim et al. |
| 2013/0017239 A1 | 1/2013 | Viladot Petit et al. |
| 2013/0034596 A1 | 2/2013 | Apert et al. |
| 2013/0039862 A1 | 2/2013 | Malle et al. |
| 2013/0045197 A1 | 2/2013 | Chavan et al. |
| 2013/0052185 A1 | 2/2013 | Kim et al. |
| 2013/0053422 A1 | 2/2013 | Edmonds et al. |
| 2013/0071470 A1 | 3/2013 | Aburdeineh |
| 2013/0089524 A1 | 4/2013 | Petit et al. |
| 2013/0115317 A1 | 5/2013 | Charbonneau et al. |
| 2013/0129653 A1 | 5/2013 | Castiel et al. |
| 2013/0149257 A1 | 6/2013 | Giori et al. |
| 2013/0230609 A1 | 9/2013 | Modak |
| 2013/0251695 A1 | 9/2013 | Farmer et al. |
| 2013/0287708 A1 | 10/2013 | Silberstein et al. |
| 2013/0302298 A1 | 11/2013 | Chevalier et al. |
| 2013/0323335 A1 | 12/2013 | Rozenblat et al. |
| 2014/0004165 A1 | 1/2014 | Novejarque et al. |
| 2014/0004214 A1 | 1/2014 | Kedrowski et al. |
| 2014/0023693 A1 | 1/2014 | Guenzburg et al. |
| 2014/0037688 A1 | 2/2014 | Berkes et al. |
| 2014/0065209 A1 | 3/2014 | Putaala et al. |
| 2014/0065210 A1 | 3/2014 | Koenig et al. |
| 2014/0065218 A1 | 3/2014 | Lang et al. |
| 2014/0073009 A1 | 3/2014 | Joergensen et al. |
| 2014/0079657 A1 | 3/2014 | Resnick et al. |
| 2014/0094525 A1 | 4/2014 | Snyder et al. |
| 2014/0099270 A1 | 4/2014 | Fu et al. |
| 2014/0186409 A1 | 7/2014 | Lang et al. |
| 2014/0193888 A1 | 7/2014 | Souter et al. |
| 2014/0205651 A1 | 7/2014 | Forsgren-Brusk et al. |
| 2014/0242198 A1* | 8/2014 | Modak .................. A01N 31/08 424/736 |
| 2014/0243423 A1 | 8/2014 | Gurge |
| 2014/0271877 A1 | 9/2014 | Wilmott et al. |
| 2014/0301994 A1 | 10/2014 | Klapper et al. |
| 2014/0308258 A1 | 10/2014 | Matthews |
| 2014/0308375 A1 | 10/2014 | Willimann |
| 2014/0322151 A1 | 10/2014 | Fricke et al. |
| 2014/0335043 A1 | 11/2014 | Chon et al. |
| 2014/0342437 A1 | 11/2014 | Barnes et al. |
| 2014/0349375 A1 | 11/2014 | Benjamin et al. |
| 2014/0356295 A1* | 12/2014 | Gerardi ................. A61K 36/81 424/43 |
| 2014/0356296 A1 | 12/2014 | Stoer |
| 2014/0364509 A1 | 12/2014 | Wegner et al. |
| 2015/0024072 A1 | 1/2015 | Chon et al. |
| 2015/0024073 A1 | 1/2015 | Chon et al. |
| 2015/0024074 A1 | 1/2015 | Batchvarova et al. |
| 2015/0024077 A1 | 1/2015 | Batchvarova et al. |
| 2015/0044317 A1 | 2/2015 | Farmer et al. |
| 2015/0073051 A1 | 3/2015 | Cohen et al. |
| 2015/0079040 A1 | 3/2015 | O'Neill et al. |
| 2015/0093462 A1 | 4/2015 | Yarosh et al. |
| 2015/0148309 A1 | 5/2015 | Riccio |
| 2015/0202136 A1 | 7/2015 | Lanzalaco et al. |
| 2015/0209392 A1 | 7/2015 | Song et al. |
| 2015/0258003 A1 | 9/2015 | Copeland et al. |
| 2015/0265666 A1 | 9/2015 | Modak et al. |
| 2015/0290273 A1 | 10/2015 | Botto et al. |
| 2015/0305343 A1 | 10/2015 | Burke et al. |
| 2015/0320038 A1 | 11/2015 | Marthaler |
| 2015/0320809 A1 | 11/2015 | Carpenter et al. |
| 2015/0353870 A1 | 12/2015 | Lant |
| 2015/0374607 A1 | 12/2015 | Lanzalaco et al. |
| 2016/0000845 A1 | 1/2016 | Olsen |
| 2016/0008412 A1 | 1/2016 | Putaala et al. |
| 2016/0040119 A1 | 2/2016 | Hashman |
| 2016/0053240 A1 | 2/2016 | Olinski et al. |
| 2016/0074312 A1 | 3/2016 | Msika et al. |
| 2016/0074460 A1 | 3/2016 | Deo |
| 2016/0158144 A1 | 6/2016 | Gan |
| 2016/0279075 A1 | 9/2016 | Redmond |
| 2017/0281660 A1 | 10/2017 | Zapka |

(56) References Cited

U.S. PATENT DOCUMENTS

| | | |
|---|---|---|
| 2017/0281694 A1 | 10/2017 | Gantz |
| 2017/0281695 A1 | 10/2017 | Gantz |
| 2017/0281718 A1 | 10/2017 | Hudson |
| 2018/0140527 A1 | 5/2018 | Hudson |
| 2018/0140539 A1 | 5/2018 | Gantz |
| 2018/0140540 A1 | 5/2018 | Gantz |
| 2018/0140545 A1 | 5/2018 | Hudson |

FOREIGN PATENT DOCUMENTS

| | | | |
|---|---|---|---|
| CN | 101129311 A | | 2/2008 |
| CN | 102000009 B | * | 6/2012 |
| CN | 103599051 A | | 2/2014 |
| CN | 104274357 A | | 1/2015 |
| CN | 104666285 A | | 6/2015 |
| CN | 104997674 A | | 10/2015 |
| CN | 105106062 A | | 12/2015 |
| CN | 105482915 A | | 4/2016 |
| DE | 102004011968 A1 | | 9/2005 |
| DE | 102011009798 A1 | | 8/2012 |
| DE | 102012002592 A1 | | 8/2013 |
| DE | 102013225844 A1 | | 6/2015 |
| EP | 1060745 A2 | | 12/2000 |
| EP | 2081606 | | 2/2002 |
| EP | 1594554 B1 | | 7/2004 |
| EP | 1736537 A1 | | 12/2006 |
| EP | 1438072 B1 | | 5/2008 |
| EP | 1920774 A1 | | 5/2008 |
| EP | 1911494 A3 | | 7/2008 |
| EP | 1965765 A2 | | 9/2008 |
| EP | 1344528 B1 | | 10/2008 |
| EP | 1455802 B1 | | 10/2008 |
| EP | 1778258 B1 | | 1/2009 |
| EP | 2019133 A1 | | 1/2009 |
| EP | 1602377 A4 | | 6/2009 |
| EP | 1296701 B1 | | 9/2009 |
| EP | 1311238 B1 | | 10/2009 |
| EP | 1529097 B1 | | 10/2009 |
| EP | 1787651 B1 | | 2/2010 |
| EP | 1301078 B1 | | 3/2010 |
| EP | 1672015 B1 | | 11/2010 |
| EP | 2305212 A1 | | 4/2011 |
| EP | 2308566 A1 | | 4/2011 |
| EP | 1353631 B1 | | 9/2011 |
| EP | 2364712 A1 | | 9/2011 |
| EP | 2430135 | | 3/2012 |
| EP | 2441433 A1 | | 4/2012 |
| EP | 1739095 A4 | | 8/2012 |
| EP | 2556823 A2 | | 2/2013 |
| EP | 2929873 A1 | | 10/2015 |
| FR | 2908306 A1 | | 5/2008 |
| FR | 2912055 A1 | | 8/2008 |
| FR | 2916634 A1 | | 12/2008 |
| FR | 2930155 A1 | | 10/2009 |
| FR | 2937548 A1 | | 4/2010 |
| FR | 2938768 A1 | | 5/2010 |
| FR | 2940098 A1 | | 6/2010 |
| FR | 2942720 A1 | | 9/2010 |
| FR | 2956818 A1 | | 9/2011 |
| FR | 2959126 A1 | | 10/2011 |
| FR | 2963560 A3 | | 2/2012 |
| FR | 2968990 A1 | | 6/2012 |
| FR | 2973381 A1 | | 10/2012 |
| FR | 3040624 A1 | | 3/2017 |
| GB | 2391476 A | | 2/2004 |
| GB | 2466195 A | | 6/2010 |
| GB | 2472790 A | | 2/2011 |
| JP | H069349 A | | 1/1994 |
| JP | H06287106 A | | 10/1994 |
| JP | 2000143513 A | | 5/2000 |
| JP | 20071786505 A | | 7/2007 |
| JP | 2008099632 A | | 5/2008 |
| JP | 2008105983 A | | 5/2008 |
| JP | 2008179595 A | | 8/2008 |
| JP | 2008179601 A | | 8/2008 |
| JP | 2008194026 A | | 8/2008 |
| JP | 2008212111 A | | 9/2008 |
| JP | 2009084228 A | | 9/2008 |
| JP | 2008308478 A | | 12/2008 |
| JP | 2009143860 A | | 7/2009 |
| JP | 2009144165 A | | 7/2009 |
| JP | 2009242309 A | | 10/2009 |
| JP | 2009292808 A | | 12/2009 |
| JP | 2010006757 A | | 1/2010 |
| JP | 2010126484 A | | 6/2010 |
| JP | 2010132629 A | | 6/2010 |
| JP | 2010143885 A | | 7/2010 |
| JP | 2010150240 A | | 7/2010 |
| JP | 2010270152 A | | 12/2010 |
| JP | 2011168520 A | | 9/2011 |
| JP | 2011195537 A | | 10/2011 |
| JP | 2011195601 A | | 10/2011 |
| JP | 2011195843 A | | 10/2011 |
| JP | 2012188453 A | | 10/2012 |
| KR | 2010130094 A | | 12/2010 |
| KR | 2011026237 A | | 3/2011 |
| PL | 219328 B1 | | 4/2015 |
| WO | 1997049793 A2 | | 12/1997 |
| WO | 1998047374 A1 | | 10/1998 |
| WO | 2000006116 A1 | | 2/2000 |
| WO | 2001013927 A2 | | 3/2001 |
| WO | 2002045727 A1 | | 6/2002 |
| WO | 2004055041 A2 | | 4/2003 |
| WO | 2003086274 A2 | | 10/2003 |
| WO | 2004055041 A2 | | 7/2004 |
| WO | 2005016364 A1 | | 2/2005 |
| WO | 2005027893 A1 | | 3/2005 |
| WO | 2006015726 A1 | | 2/2006 |
| WO | 2006104403 A1 | | 10/2006 |
| WO | 2006118942 A2 | | 11/2006 |
| WO | WO-2006118942 A2 | * | 11/2006 ............. A61K 8/898 |
| WO | 2008021441 A2 | | 2/2008 |
| WO | 2008047908 A1 | | 4/2008 |
| WO | 2008015343 A3 | | 5/2008 |
| WO | 2008040516 A3 | | 5/2008 |
| WO | 2008114376 A1 | | 9/2008 |
| WO | 2008146116 A2 | | 12/2008 |
| WO | 2008148694 A1 | | 12/2008 |
| WO | 2009017463 A2 | | 2/2009 |
| WO | 2009031099 A2 | | 3/2009 |
| WO | 2009050677 A2 | | 4/2009 |
| WO | 2009053564 A2 | | 4/2009 |
| WO | 2009066537 A1 | | 5/2009 |
| WO | 2009077749 A1 | | 6/2009 |
| WO | 2009086614 A1 | | 7/2009 |
| WO | 2009087356 A1 | | 7/2009 |
| WO | 2009095456 A1 | | 8/2009 |
| WO | 2009127057 A1 | | 10/2009 |
| WO | 2009141542 A2 | | 11/2009 |
| WO | 2009141544 A2 | | 11/2009 |
| WO | 2010013182 A1 | | 2/2010 |
| WO | 2010061383 A1 | | 6/2010 |
| WO | 2010087373 A1 | | 8/2010 |
| WO | 2010126414 A1 | | 11/2010 |
| WO | 2010128906 A1 | | 11/2010 |
| WO | 2010130541 A1 | | 11/2010 |
| WO | 2011019668 A1 | | 2/2011 |
| WO | 2011029784 A1 | | 3/2011 |
| WO | 2011048554 A2 | | 4/2011 |
| WO | 2011061144 A2 | | 5/2011 |
| WO | 2011064524 A1 | | 6/2011 |
| WO | 2011065772 A1 | | 6/2011 |
| WO | 2011073437 A2 | | 6/2011 |
| WO | 2011117547 A1 | | 9/2011 |
| WO | 2011130788 A1 | | 10/2011 |
| WO | 2011157968 A1 | | 12/2011 |
| WO | 2011158027 A1 | | 12/2011 |
| WO | 2012000960 A1 | | 1/2012 |
| WO | 2012000961 A1 | | 1/2012 |
| WO | 2012000963 A1 | | 1/2012 |
| WO | 2012013764 A2 | | 1/2012 |
| WO | 2012013776 A2 | | 1/2012 |
| WO | 2012022478 A2 | | 2/2012 |
| WO | 2012022773 A1 | | 2/2012 |

(56) References Cited

FOREIGN PATENT DOCUMENTS

| | | |
|---|---|---|
| WO | 2012049697 A1 | 4/2012 |
| WO | 2012055408 | 5/2012 |
| WO | 2012062895 A1 | 5/2012 |
| WO | 2012067321 A1 | 5/2012 |
| WO | 2012071654 A1 | 6/2012 |
| WO | 2012072951 A1 | 6/2012 |
| WO | 2012076321 A1 | 6/2012 |
| WO | 2012082065 A1 | 6/2012 |
| WO | 2012084701 A2 | 6/2012 |
| WO | 2012107550 A2 | 8/2012 |
| WO | 2012118535 A1 | 9/2012 |
| WO | 2012120290 A2 | 9/2012 |
| WO | 2012129683 | 10/2012 |
| WO | 2012149110 A1 | 11/2012 |
| WO | 2012150269 A1 | 11/2012 |
| WO | 2012152270 A1 | 11/2012 |
| WO | 2012160289 A2 | 11/2012 |
| WO | 2013000717 A2 | 1/2013 |
| WO | 2013050697 A2 | 4/2013 |
| WO | 2013068962 A2 | 5/2013 |
| WO | 2013073431 A1 | 5/2013 |
| WO | 2013087665 A2 | 6/2013 |
| WO | 2013089720 A1 | 6/2013 |
| WO | 2013100003 A1 | 7/2013 |
| WO | 2013120481 A2 | 8/2013 |
| WO | 2013122931 A2 | 8/2013 |
| WO | 2013130829 A1 | 9/2013 |
| WO | 2013149323 | 10/2013 |
| WO | 2013171343 A2 | 11/2013 |
| WO | 2013188626 | 12/2013 |
| WO | 2013190542 | 12/2013 |
| WO | 2014043304 | 3/2014 |
| WO | 2014044957 A1 | 3/2014 |
| WO | 2014064397 A1 | 5/2014 |
| WO | 2014107572 A1 | 7/2014 |
| WO | 2014131191 A1 | 9/2014 |
| WO | 2014155111 | 10/2014 |
| WO | 2014162125 A1 | 10/2014 |
| WO | 2014197168 A1 | 12/2014 |
| WO | 2015000972 | 1/2015 |
| WO | 2015075440 | 5/2015 |
| WO | 2015089441 | 6/2015 |
| WO | 2015106175 A1 | 7/2015 |
| WO | 2015120100 | 8/2015 |
| WO | 2015124943 | 8/2015 |
| WO | 2015138296 A1 | 9/2015 |
| WO | 2015138479 A1 | 9/2015 |
| WO | 2015143360 A1 | 9/2015 |
| WO | 2015151009 | 10/2015 |
| WO | 2015171899 A1 | 11/2015 |
| WO | 2015185689 A1 | 12/2015 |
| WO | 2015189049 | 12/2015 |
| WO | 2016172686 | 12/2015 |
| WO | 2016007314 A1 | 1/2016 |
| WO | 2016161074 A2 | 10/2016 |
| WO | 2017173236 A1 | 10/2017 |
| WO | 2017173240 A1 | 10/2017 |
| WO | 2017173241 A1 | 10/2017 |
| WO | 2017173242 A1 | 10/2017 |

OTHER PUBLICATIONS

Anonymous, "Ashland Care Specialties Announces Skin's Ecology, An Initiative for Probiotic Effects—Produktneuheiten—SOFW" Retrieved from the Internet: URL: http://www.sofw.com/index/sofw_de/sofw de_produktneuhei ten. html ?naid=5133 retrieved on Jun. 8, 2017] the whole document. Mar. 5, 201.

Gaurav Kaithwas et al., "Linum Usitati ssimum (Linseed/Flaxseed) Fixed Oil: Antimicrobial Activity and Efficacy in Bovine Mastitis", Inflamm0pharmac0l0gy, Kluwer Academic Publishers, Dordrecht, NL, vol. 19, No. 1, Feb. 1, 2011, pp. 45-52.

Fehlbaum P et al., "An Essential Amino Acid Induces Epithelial Beta-Defnsin Expression," Proceedings National Academy of Sciences PNAS, National Academy of Sciences, US, vol. 97, No. 23, Nov. 7, 2000, pp. 12723-12728.

International Search Report and Written Opinion from PCT/US2017/025329 dated Jul. 21, 2017.

Kimble et al., "Use of a Fluorometric Microplate Assay to Assess the Activty of Prebiotics and Probiotics Against Uropathogenic E. coli Adherence to Human Uroepithelial Cells," FASEB Journal, vol. 29, No. Suppl 1, Apr. 1, 2015, p. 607.9.

Rousseau et al., "Prebiotic Effects of Oligosaccharides on Selected Vaginal Lactobacilli and Pathogenic Microorganisms," ANAE London, GB, vol. 11, No. 3, Jun. 1, 2005, pp. 145-153.

Shoaf K et al., "Prebiotic Galactooligosaccharides Reduce Adherence of Enteropathogenic Escherichia coli to Tissue Culture Cells," Infection and Immunity, American Society for Microbiology, vol. 74, No. 12, Dec. 1, 2006, pp. 6920-6928.

Invitation to Pay Additional Fees from PCT/US2017/062766 dated Feb. 26, 2018.

International Search Report and Written Opinion from PCT/US2017/062797 dated Feb. 19, 2018.

International Search Report and Written Opinion from PCT/US2017/062807 dated Mar. 2, 2018.

International Search Report and Written Opinion from PCT/US2017/062784 dated Feb. 22, 2018.

Dong Z et al., Composition, Useful for Cleaning Hair, Comprises Chichona Tree Tincture, Saponin Tincture, Eucalyptus Tincture, Flaxseed Extract, Ethyl Alcohol, and Active Comonent Comprising Vitamin E, Ectoine and Vitamin B5, Clarivate Analytics, vol. 2015, No. 27, Jan. 14, 2015 Abstract.

Hill et al., The International Scientic Association for Probiotics and Prebiotics Consensus Statement on the Scope and Apprpriate Use of the Term Proboiotic, Expert Consensus Document, Nature Reviews/Gastroenterology & Hepatology, vol. 11, No. 8, Aug. 1, 2015, pp. 506-514.

Hutkins et al., "Prebiotics: Why Definitions Matter," Current Opinion in Biotechnology, vol. 37, Sep. 29, 2015, pp. 1-7.

Mintel, "Baby's Body Wash" Apr. 2014 XP002777898.

Mintel, "Body Wash" Dec. 2009 XP002777900.

Mintel, "Moisturizing Body Wash" Jan. 2013 XP002777899.

Jimborean et al. "Use of Essential Oils from Citrus sinensis in the Development of New Type of Yogurt", Bulletin of University of Agricultural Sciences and Veterinary Medicine Cluj-Napoca. Food Science and Technology, vol. 73, No. 1, May 1, 2016.

Mintel, "Shower Gel" Jul. 2016 XP002777896.

Mintel, "Shower Gel" Nov. 2014 XP002777897.

Mintel; "Hand Gel" Nov. 2014 XP002777823, retrieved from www.gnpd.com.

Bockmuhl, D. et al. "Prebiotic Cosmetics: An Alternative to Antibacterial Products," Int'l J of Cosmetic Sci., vol. 29, Issue 1, Feb. 13, 2007 Abstract.

Eishaghbee et al., "Ethanol Production by Selected Intestinal Microorganisms and Lactic Acid Bacteria Growing Under Different Nutritional Conditions," Frontiers in Microbiology, Original Research, Jan. 2016, vol. 7, Article 47, pp. 1-13.

Karamac et al., "Antioxidant Activity of Hydrolysates Prepared From Flaxseed Cake Proteins Using Pancreatin," Pol. J. Food Nutr. Sci., 2014, vol. 64, No. 4, pp. 227-233.

Lactic Acid, Skin Deep Cosmetic Database, EWG, 2019.

Marambe, et al., An In-Vitro Investigation of Selected Biological Activities of Hydrolysed Flaxseed (Linum usitatissimum L.) Proteins, J Am Oil Chem Soc, 2008, vol. 85, pp. 1155-1164.

Ohara et al., "L-Lactic Acid Production by Bacillus sp. In Anaerobic and Aerobic Culture," Journal of Fermentation and Bioengineering, vol. 81, No. 3, pp. 272-274, 1996.

Shim et al., "Flaxseed (Linum usitatissim Um L.) Bioactive Compound and Peptide Nomenclature: A Review" Trends in Food Science & Technology, vol. 38, Issue 1, Jul. 2014, pp. 5-20.

Branco, C. et al. "Modulation of Skin Microbiota by Topical Prebiotics", Monographic Supplement Series: Skin Care—Household and Personal Care Today, vol. 10(2) Mar./Apr. 2015, p. 21-27.

Lucera et al., Food Applicatons of Natural Antimicrobial Compounds, Frontiers in Microbiology, vol. 3, p. 1-13, Aug. 8, 2012.

(56) References Cited

OTHER PUBLICATIONS

Ueda et al., "Topical and Transdermal Drug Products," Pharmacopeial Forum, vol. 35(3); pp. 750-764, May-Jun. 2009.
https://en.wikipedia.org/wiki/Clostridium (Year: 2020).
https://en.wikipedia.org/wiki/Escherichia_coli (Year: 2020).
https://en.wikipedia.org/wiki/Lactobacillus (Year: 2020).
https://en.wikipedia.org/wiki/Saccharomyces (Year: 2020).

* cited by examiner

ANTIMICROBIAL PEPTIDE STIMULATING CLEANSING COMPOSITION

RELATED APPLICATIONS

This application claims priority to and the benefit of U.S. Provisional Patent Application Ser. No. 62/316,123, entitled "ANTIMICROBIAL PEPTIDE STIMULATING CLEANSING COMPOSITION" and filed Mar. 31, 2016, the entire disclosure of which is incorporated herein by reference.

BACKGROUND

Skin disinfecting and cleansing compositions have become increasingly popular in the health care industry as well as with the general public for providing antimicrobial effectiveness to the skin without irritation.

Recent microbiome studies have analyzed the chemical make-up of the skin and the potential for disinfecting and cleansing compositions to improve both skin defense against germs and skin's innate immunity. This includes germ control through both internal and external methods. External methods include hygiene products that directly kill or slow germ growth. Internal methods include improving an organism's immune system to fight germs itself.

Antimicrobial peptides ("AMPs"), also known as host defense peptides, comprise a wide range of natural and synthetic peptides that are made of oligopeptides containing a varying number of amino acids. AMPs are essential components of host defense against infections present in all domains of life. AMPs are produced by all complex organisms and have diverse and intricate antimicrobial activities. As a whole, these peptides demonstrate a broad range of antiviral and antibacterial activities through an array of modes of action. AMPs have been found to kill Gram-negative and Gram-positive bacteria, certain viruses, parasites and fungi. Some research suggests that they can also enhance the internal immunity of complex organisms against a broad range of bacteria and viruses. In addition to the innate immune system present in all animals, vertebrates evolved an adaptive immune system based on specific recognition of antigens. Increasing evidence suggests that AMPs released in response to an invasion of microbial can activate adaptive immunity by attracting antigen-presenting dendritic cells to the invasion site.

While traditional soap and lotion formulations can stimulate the production of AMPs on the skin, the levels thereof are not sufficient to produce the desired effects of long lasting germ defense and innate immunity on the skin. It is thus desirable to design a new soap and/or lotion composition that is safe for topical use that stimulates the production AMPs to levels that help the skin fight germs and maintain continued immunity.

SUMMARY

Some exemplary embodiments are directed to a topical cleansing composition for stimulating the production of antimicrobial peptides on the skin. The composition comprises about 0.02 wt. % to about 10.0 wt. % of an active ingredient, at least about 1.0 wt. % of one or more surfactants, and water. The active ingredient comprises one or more of a natural extract and a polypeptide. The topical composition increases the concentration of antimicrobial peptides on skin, as compared to an otherwise identical topical composition without the active ingredient.

In some exemplary embodiments, the natural extract is one or more of a plant extract, a seed extract and a fruit extract. The seed extract may be at least one of linseed extract, flaxseed extract, hemp seed extract, grape seed extract, and grapefruit seed extract.

In some exemplary embodiments, the active ingredient is a polypeptide, such as at least one of an oligopeptide and a hexapeptide.

In some exemplary embodiments, the topical cleansing composition comprises about 0.05 to about 5.0 wt. %, or about 0.1 to about 1.0 wt. % active ingredient, based on the weight of the total composition.

Some exemplary embodiments of the present topical cleansing composition include one or more surfactants selected from the group consisting of betaines such as cocamidoproyl betaine, sulfonates and sulfates such as sodium laureth sulfate or alkylbenzene sulfonates, cocamidopropyl hydroxysultaine, lauryl gluocoside, PEG-80 sorbitan laurate, di-alkyl sulfosuccinate, lignosulfonates, disodium cocoamphodiacetate, lauryl glucoside, and PEG-80 sodium laurate. In some exemplary embodiments, the topical cleansing composition comprises at least one primary surfactant and at least one secondary surfactant. In some exemplary embodiments, the primary surfactant is sodium, laureth sulfate. In some exemplary embodiments, the primary surfactant is one or more of cocamidopropyl betaine, disodium cocoamphodiacetate, cocamidopropyl hydroxysultaine, and lauryl glucoside.

In some exemplary embodiments, the topical composition comprises one or more humectants, selected from the group consisting of propylene glycol, hexylene glycol, 1,4-dihydroxyhexane, 1,2,6-hexanetriol, sorbitol, butylene glycol, caprylyl glycol, propanediols, such as methyl propane diol, dipropylene glycol, triethylene glycol, glycerin (glycerol), polyethylene glycols, ethoxydiglycol, polyethylene sorbitol, and combinations thereof. The humectant may be present in an amount up to about 20.0 wt. %, based on the weight of the total composition.

The topical composition increases antimicrobial peptide concentration by a statistically significant amount, as compared to an otherwise identical composition without the active ingredient. In some exemplary embodiments, the topical composition increases the concentration of HBD-1 by at least about 10%, relative to an otherwise identical topical composition without said active ingredient. In some exemplary embodiments, the topical composition increases the concentration of HBD-2 by at least about 5%, relative to an otherwise identical topical composition without said active ingredient. In some exemplary embodiments, the topical composition increases the concentration of HBD-3 by at least about 5%, relative to an otherwise identical topical composition without said active ingredient. In some exemplary embodiments, the topical composition increases the concentration of LL-37 by at least about 5%, relative to an otherwise identical topical composition without said active ingredient.

In various exemplary embodiments, the topical composition decreases the concentration of IL-8 by at least about 5%, relative to an otherwise identical topical composition without said active ingredient.

Some exemplary embodiments are directed to a method of skin treatment to increase the production of antimicrobial peptides on the skin. The method comprises applying a topical cleansing composition to a skin surface, wherein the topical composition includes about 0.02 wt. % to about 10.0 wt. % of an active ingredient and at least about 1.0 wt. % of one or more surfactants, with the balance up to 100 wt. % being water. The active ingredient comprises one or more of a natural extract and a polypeptide. The topical composition increases the concentration of antimicrobial peptides on skin, as compared to an otherwise identical topical soap composition without the active ingredient. The method further includes washing the cleansing composition off with water.

Some exemplary embodiments are directed to a skin treatment composition comprising about 0.02 wt. % to about 10.0 wt. % of an active ingredient comprising one or more of a natural extract and a polypeptide, at least about 1.0 wt. % of one or more surfactants, and about 0.01 wt. % to about 10.0 wt. % of a humectant, with the balance up to 100 wt. % being water.

Further exemplary embodiments are directed to a topical lotion composition for increasing the innate immunity of the skin comprising about 0.02 wt. % to 10.0 wt. % of an active ingredient comprising one or more of a natural extract and a polypeptide, at least about 0.1 wt. % of an oil, and about 0.01 wt. % to about 5.0 wt. % of a viscosity modifier, with the balance up to 100% being water.

DETAILED DESCRIPTION

Figure 1:
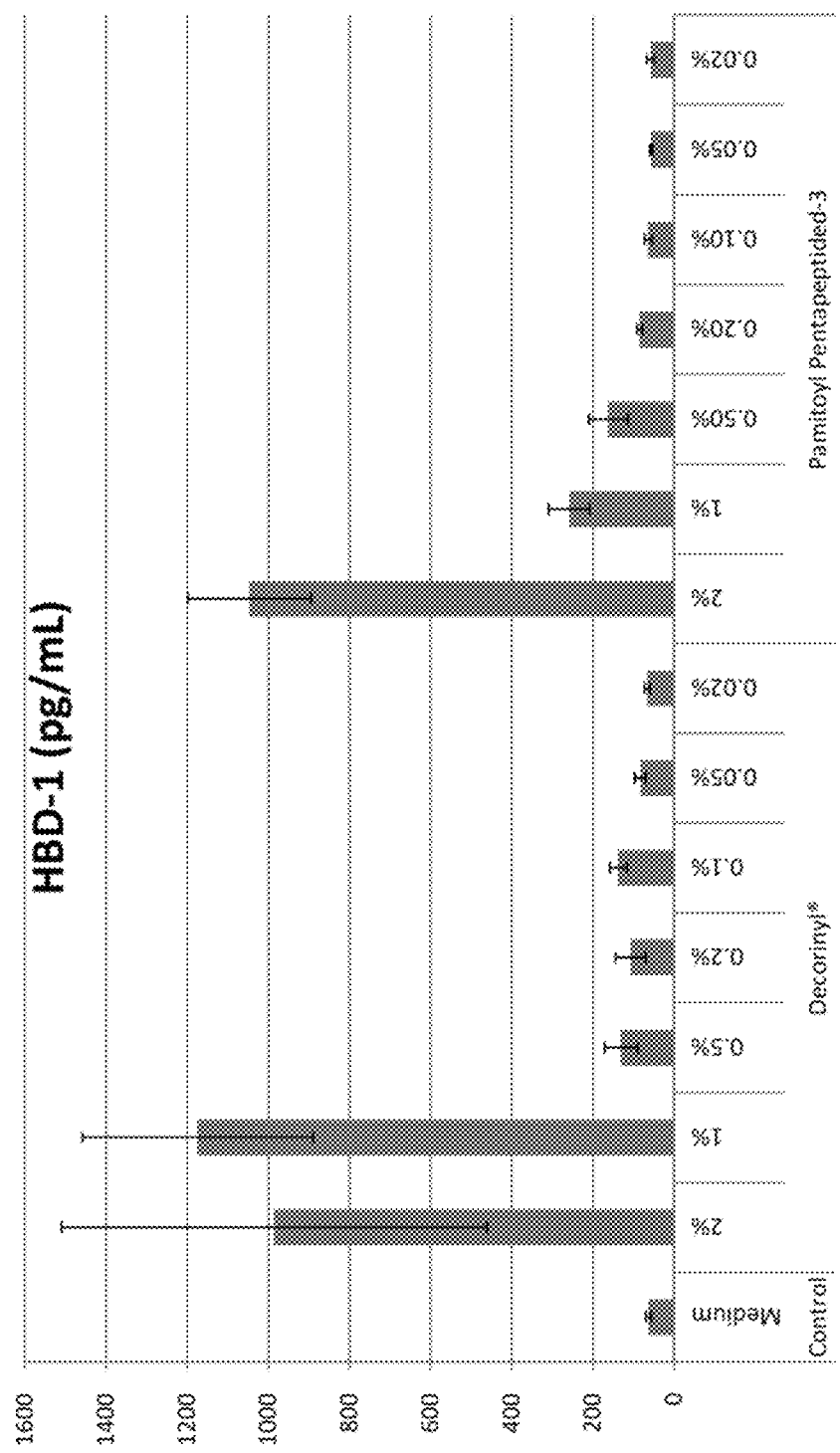
FIG. 1 graphically illustrates HBD-1 concentrations after treatment with various concentrations of Decorinyl and Pamitoyl Pentapeptide-3.

Unless otherwise defined, all technical and scientific terms used herein have the same meaning as commonly understood by one of ordinary skill in the art to which this application pertains. Although other methods and materials similar or equivalent to those described herein may be used in the practice or testing of the exemplary embodiments, exemplary suitable methods and materials are described below. In case of conflict, the present specification including definitions will control. In addition, the materials, methods, and examples are illustrative only and not intended to be limiting of the general inventive concepts.

The terminology as set forth herein is for description of the exemplary embodiments only and should not be construed as limiting the application as a whole. Unless otherwise specified, "a," "an," "the," and "at least one" are used interchangeably. Furthermore, as used in the description of the application and the appended claims, the singular forms "a," "an," and "the" are inclusive of their plural forms, unless contradicted by the context surrounding such.

The phrase "statistically significant" means $p<0.05$ for a test composition vs. a control that does not contain the active ingredient. The analysis is completed using 1) a T-test (a statistical examination of two population means) when only comparing one test article vs. one control); or 2) an analysis of variance (ANOVA) test when comparing two or more test articles vs. controls.

The phrase "topical composition" means a composition suitable for application directly to a surface, such as the surface of a human or animal body, including skin, and/or other surfaces, such as hair and nails.

The terms "polypeptide" and "polypeptides" as used herein refer to a chain of amino acids with two or more peptide bonds. In this way, these terms are meant to encompass both oligopeptides (which are generally considered to be peptide chains with between two and ten amino acids) as well as polypeptides (which are generally considered to be peptide chains with more than 10 amino acids).

The general inventive concepts relate to a topical composition that contains an AMP-stimulating active ingredient, including a natural extract and/or one or more polypeptides. The introduction of the active ingredient. In some exemplary embodiments, the active ingredient is derived from a natural extract, such as a plant extract, a fruit extract, and/or a seed extract, produced from the hydrolysis of natural proteins. Thus, the natural extracts may themselves comprise one or more peptides and/or polypeptides or the active ingredient may comprise polypeptide(s) independently. Non-limiting examples of natural extracts may include seed extracts, fruit extracts, linseed extract, flaxseed extract, hemp seed extract, grape seed extract, grapefruit seed extract, watermelon fruit extract, apple fruit extract, lentil fruit extract, hibiscus flower extract, pear fruit extract, root extract, leaf extract, *Schinus terebinthifolius* Seed Extract, *Ascophyllum nodosum* extract, soybean extract, *Crothmum martimum* extract, *Lavandula stoechas* extract, stem extracts, *Sapindus Mukurossi* fruit extract, sandalwood extract, bark extract, barley extract, *Polygonum fagopyrum* seed extract, avocado extract, cranberry fruit extract, blueberry fruit extract, *Silena uniforla* extract, *Rosa multiflora* extract, *Evodia rutaecarpa* fruit extract, algae extract, licorice leaf extract, jobi seed extract, seed oils, rosemary extract, green tea extract, plankton extract, himanthalia elongata extract, unidaria pinnatifida extract, *Chlorella vulgaris* extract, mugwort extract, and the like.

In some exemplary embodiments, the natural extract is selected from one or more of the following compositions: (1) glycerin, plantago lanceolata leaf extract and xanthan gum (sold under the trade name Senestem™ by Sederma); (2) Benoitine (plankton extract in water); (3) water, glycerin, and hydrolyzed pearl (sold under the trade name Crodarom® by Croda Inc.) (4) *Red Bush* (rooibos) plant extract, (5) Phyko-Al-PF (water and hydrolyzed algin), and water, glycerin, and linseed (*linum usitatissimum*) seed extract (sold under the trade name Lipigenine™ by Ashland Chemical Company).

In some exemplary embodiments, the active ingredient comprises one or more amino acids. Amino acids are organic compounds containing amine and carboxylic acid functional groups. The amino acid can be an alpha, beta, gamma, or delta amino acid and can be in either enantiomer (L or D isomer). The amino acids of the present invention are not particularly limited and can include, but are not limited to, histidine, isoleucine, leucine, lysine, methionine, phenylalanine, threonine, tryptophan, valine, alanine, arginine, asparagine, aspartic acid, cysteine, glutamic acid, glutamine, glycine, proline, selenocystenine, serine, and tyrosine.

In some exemplary embodiments, the active ingredient comprises one or more peptides. Peptides are biologically-occurring short chains of amino acid monomers joined together by amide (peptide) bonds, which are formed through condensation reactions.

In other exemplary embodiments, the active ingredient comprises one or more oligopeptides. Oligopeptides are generally defined as peptide chains with 10 or fewer amino acids. In this way, the oligopeptide may be include, but is not limited to, an oligopeptide, such as a dipeptide, a tripeptide, a tetrapeptide, a pentapeptide, a hexapeptide, a heptapeptide, an octapeptide, a nonapeptide, and a decapeptide.

In other exemplary embodiments, the active ingredient comprises one or more polypeptides. A polypeptide is a long, continuous, unbrached peptide chain. Polypeptides are generally defined as peptide chains with more than 10 amino acids. The polypeptides of the present invention are not particularly limited and can be made of any number of peptide bonds.

In other exemplary embodiments, the active ingredient comprises a protein, which includes at least one long polypeptide that is arranged in a biologically functional way. The proteins of the present invention are not particularly limited and can include any number of polypeptides arranged in any biologically active manner. The peptides, oligopeptides, polypeptides, and proteins comprising the subject topical composition can be natural or synthetic peptides or polypeptides.

Exemplary polypeptides include Juvefoxo™; tetrapeptides, such as Uplevity™, Relistase®, and Decorinyl®; pentapeptides, such as palmitoyl pentapeptide-4, palmitoyl pentapeptide-3, and acetyl pentapeptide-1; hexapeptides, such as Adifyline® and acetyl hexapeptides; and mixtures of polypeptides and natural extracts, such as Triple A Complex, Trylagen® PCB. Exemplary acetyl hexapeptides include acetyl hexapeptide-1, acetyl hexapeptide-3, acetyl hexapeptide-7, acetyl hexapeptide-8, acetyl hexapeptide-19, acetyl hexapeptide-20, acetyl hexapeptide-22, acetyl hexapeptide-24, acetyl hexapeptide-30, acetyl hexapeptide-31, acetyl hexapeptide-37, acetyl hexapeptide-38, acetyl hexapeptide-39, acetyl hexapeptide-46, and acetyl hexapeptide-49. In some exemplary embodiments, the polypeptides include two or more acetyl hexapeptides.

In some exemplary embodiments, the topical composition disclosed herein includes an effective amount of active ingredient to increase the concentration of one or more AMPS, including, for example, HBD-1, HBD-2, and HBD-3, as well as LL-37 (cathelicidin) on the surface of the skin. Such concentration increase helps the skin ability to defend against germs and helps improve the skin's innate immunity. Traditionally, it has been found that compositions used to stimulate the production of AMPS also cause skin inflammation and/or skin irritation. However, it has been discovered that a topical composition comprising the subject active ingredient is capable of increasing the concentration of AMPS on the skin without causing irritation/inflammation of the skin.

The effective amount of active ingredient in the topical composition may include up to about 10.0 percent by weight (wt. %) of the active ingredient, based upon the total weight of the composition. In some exemplary embodiments, the effective amount of active ingredient comprises about 0.02 to about 5.0 wt. %, or from about 0.5 to about 2.0 wt. %, based upon the total weight of the topical composition. In other exemplary embodiments, the effective amount of active ingredient comprises about 0.1 to about 1.0 wt. %, based upon the total weight of topical composition.

In some exemplary embodiments, the topical composition is in the form of a cleanser, such as a soap or a lotion-based cleanser and is used for application to the skin. The topical composition may be in the form of a skin cleanser, skin moisturizer, skin protectant, shampoo, a wipe, a lotion, a salve, foam, soap, gel, a cream, etc. A wide variety of vehicles may be used to deliver the topical composition, such a, for example pads, bandages, patches, sticks, aerosol dispersers, pump sprays, trigger sprays, canisters, foam pumps, wipes, and the like. The topical composition may be applied to the skin before, during, or after skin cleaning.

In some exemplary embodiments, the topical composition includes water quantum sufficil (q.s.). In some exemplary embodiments, the topical composition comprises at least about 40 weight percent (wt. %) water, in another embodiment, the topical composition comprises at least about 50.0 wt. % water, in another embodiment, the topical composition comprises at least about 60.0 wt. % water, in another embodiment, the topical composition comprises at least about 70.0 wt. % water, in another embodiment, the topical composition comprises at least about 80.0 wt. % water, and in yet another embodiment, the topical composition comprises at least about 83.0 wt. % water, and in still yet another embodiment, the topical composition comprises at least about 85.0 wt. % water. In other embodiments, the topical composition comprises from about 80.0 wt. % to about 90.0 wt. % water. In a preferred embodiment, the topical composition comprises from about 83.0 to about 87.0 wt. % water. More or less water may be required in certain instances, depending particularly on other ingredients and/or the amounts thereof employed.

In some exemplary embodiments, the topical composition includes one or more humectants. Non-limiting examples of humectants include propylene glycol, hexylene glycol, 1,4-dihydroxyhexane, 1,2,6-hexanetriol, sorbitol, butylene glycol, caprylyl glycol, propanediol s, such as methyl propane diol, dipropylene glycol, triethylene glycol, glycerin (glycerol), polyethylene glycols, ethoxydiglycol, polyethylene sorbitol, and combinations thereof. Other humectants include glycolic acid, glycolate salts, lactate salts, urea, Jojoba wax PEG-120 esters (commercially available from FloraTech), hydroxyethyl urea, alpha-hydroxy acids, such as lactic acid, sodium pyrrolidone carboxylic acid, hyaluronic acid, chitin, and the like. In one exemplary embodiment, the humecant is a mixture of caprylyl glycol, sodium L-pyroglutamate (Sodium PCA), and glycerin.

Examples of polyethylene glycol humectants include PEG-4, PEG-6, PEG-7, PEG-8, PEG-9, PEG-10, PEG-12, PEG-14, PEG-16, PEG-18, PEG-20, PEG-32, PEG-33, PEG-40, PEG-45, PEG-55, PEG-60, PEG-75, PEG-80, PEG-90, PEG-100, PEG-135, PEG-150, PEG-180, PEG-200, PEG-220, PEG-240, and PEG-800.

The humectant may be included in the topical composition in an amount up to about 20.0 wt. %, or up to about 15.0 wt. %, or up to about 12.0 wt. %, or up to about 10.0 wt. %, or up to about 8.0 wt. %, or up to about 3.0 wt. %. In some exemplary embodiments, the humectant is included in an amount from about 0.001 wt. %, or from about 0.01 wt. %, or from about 0.05 wt. %, or from about 0.1 wt. %, or from about 0.5 wt. %, or from about 0.7 wt. %, or from about 1.0 wt. %, or from about 1.5 wt. %, or from about 2.0 wt. %, based upon the total weight of the composition. In one exemplary embodiment, the humectant is included in an amount from about 0.4 to about 3.0 wt. %, or from about 1.5 to about 2.0 wt. %, based upon the total weight of the composition.

In one or more embodiments, the topical composition includes one or more skin-conditioners or emollients. Non-limiting examples of suitable skin conditioners and emollients include aloe, vitamin E, vitamin E acetate (tocopheryl acetate), Vitamin $B_3$ (niacinamide), $C_{6-10}$ alkane diols, sodium salt of pyroglutamic acid (sodium PCA), PEG-7 glyceryl cocoate, coco-glucoside and/or glyceryl oleate (Lamisoft® PO), and polyquaternium, such as polyquaternium 10 and 39.

The skin-conditioner or emollient can be included in the topical composition in an amount from about 0.001 to about 5.0 wt. %, in other embodiments, from about 0.005 to about 3.5 wt. %, or from about 0.01 to about 3.0 wt. %, or from about 0.05 to about 2.5 wt. %, or from about 0.1 to about 2.0 wt. %, or from about 0.5 to about 1.5 wt. %, based upon the total weight of the composition.

In some exemplary embodiments, the topical composition further includes a carrier component, such as a base cleaner.

The topical composition may further comprise one or more deposition enhancers. A suitable deposition enhancer works unidirectionally and will allow ingredients within the composition to penetrate deeper into the stratum corneum whilst preventing the loss of materials from the skin. Advantageously, the deposition enhancer provides a cosmetically acceptable skin feel to the formulation.

In one or more embodiments, the deposition enhancers include one or more of surfactants, bile salts and derivatives thereof, chelating agents, and sulphoxides.

Some examples of acceptable deposition enhancers include hydroxypropyl methylcellulose, dimethyl sulphoxides (DMSO), DMA, DMF, 1-dodecylazacycloheptan-2-one (azone), pyrrolidones such as 2- Pyrrolidone (2P) and N-Methyl -2- Pyrrolidone (NMP), long-chain fatty acids such as oleic acid and fatty acids with a saturated alkyl chain length of about $C_{10}$-$C_{12}$, essential oils, terpenes, terpenoids, oxazolidinones such as 4-decyloxazolidin-2-one, sodium lauryl sulfate (SLS), sodium laureate, polysorbates, sodium glyacolate, sodium deoxycholate, caprylic acid, EDTA, phospholipids, $C_{12-15}$ Alkyl Benzoate, pentylene glycol, ethoxydiglycol, polysorbate-polyethylenesorbitan-monolaurate, and lecithin.

In one or more exemplary embodiments, the deposition enhancer is a quaternary ammonium compound such as polyquaternium-6, -7, -10, -22, -37, -39, -74 or -101.

The deposition enhancer may be included in the topical composition in an amount from about 0.005 wt. % to about 10.0 wt. %, in other embodiments, from about 0.01 wt. % to about 5.0 wt. %, and in other embodiments, from about 0.05 wt. % to about 3.0 wt. %, based upon the total weight of the composition.

In one or more exemplary embodiments, the deposition enhancer comprises a hydroxy-terminated polyurethane compound chosen from polyolprepolymer-2, polyolprepolymer-14, and polyolprepolymer-15. Polyolprepolymer-2 is sometimes referred to as PPG-12/SMDI copolymer. The polyurethane compound may be present in the topical composition in an amount from about 0.005 wt. % to about 5.0 wt. %, in other embodiments, from about 0.01 wt. % to about 3.0 wt. %, and in other embodiments, from about 0.05 wt. % to about 1.0 wt. %, based upon the total weight of the composition.

The topical composition may further comprise one or more preservatives. A preservative is a natural or synthetic ingredient that can be added to personal care products to prevent spoilage, such as from microbial growth or undesirable chemical changes. Typical cosmetic preservatives are classified as natural antimicrobials, broad-spectrum preservatives, or stabilizers.

Many different types of preservatives are envisioned as being applicable in the current topical composition. Non-limiting examples of preservatives include one or more of isothiazolinones, such as methylchloroisothiazolinone and methylisothiazolinone; parabens including butylparaben, propylparaben, methylparaben and germaben II; phenoxyetyhanol and ethylhexylglycerin, organic acids such as potassium sorbate, sodium benzoate and levulinic acid; and phenoxyethanols.

The preservative can be added in the topical composition in an amount up to about 10.0 wt. %, preferably from about 0.05 wt. % to about 5.0 wt. %, more preferably from about 0.1 wt. % to about 2.0 wt. %, based on the weight of the total composition. In one exemplary embodiment, the preservative is present in an amount from about 1.0 to about 1.5 wt. %, based on the weight of the total composition.

The topical composition may further comprise one or more anti-irritants. Anti-irritants reduce signs of inflammation on the skin such as swelling, tenderness, pain, itching, or redness. There are three main types of anti-irritants, all of which are envisioned as being applicable in the subject invention: (1) compounds that operate by complexing the irritant itself, (2) compounds that react with the skin to block reactive sites preventing the irritant from reacting directly with the skin, and (3) compounds that prevent physical contact between the skin and irritant.

Some exemplary examples of suitable anti-irritants include Aloe Vera, allantoin, anion-cation complexes, aryloxypropionates, azulene, carboxymethyl cellulose, cetyl alcohol, diethyl phthalate, Emcol E607, ethanolamine, glycogen, lanolin, N-(2-Hydroxylthyl) Palmitamide, N-Lauroyl Sarcosinates, Maypon 4C, mineral oils, miranols, Myristyl lactate, polypropylene glycol, polyvinyl pyrrolidone (PVP), tertiary amine oxides, thiodioglycolic acid, and zirconia. In one exemplary embodiment, the anti-irritant is avenanthrmides (avena sativa (oat), kernel oil, and glycerin) and niacinamide.

The anti-irritant may be included in the topical composition in an amount up to about 10.0 wt. %, in other embodiments, from about 0.005 wt. % to about 3.0 wt. %, and in other embodiments, from about 0.01 wt. % to about 1.0 wt. %, based upon the total weight of the composition.

The topical composition may further comprise a fragrance. Any scent may be used in the topical composition including, but not limited to, any scent classification on a standard fragrance chart, such as floral, oriental, woody, and fresh. Exemplary scents include cinnamon, clove, lavender, peppermint, rosemary, thyme, thieves, lemon, citrus, coconut, apricot, plum, watermelon, ginger and combinations thereof.

The fragrance can be included in the topical composition in an amount from about 0.005 wt. % to about 5.0 wt. %, in other embodiments, from about 0.01 wt. % to about 3.0 wt. %, and in other embodiments, from about 0.05 wt. % to about 1.0 wt. %, based upon the total weight of the composition. The fragrance can be any made of any perfume, essential oil, aroma compounds, fixatives, terpenes, solvents, and the like. In some exemplary embodiments, the essential oils may include, for example, one or more of Limonene, Citrus Aurantium Dulcis (Orange) Peel Oil, Eucalyptus Globulus Leaf Oil, Citrus Grandis (Grapefruit) Peel Oil, Linalool, Litsea Cubeba Fruit Oil, Lavandula Hybrida Oil, Abies Sibirica Oil, Mentha Citrata Leaf Extract, Coriandrum Sativum (Coriander) Fruit Oil, Piper Nigrum (Pepper) Fruit Oil, and Canarium Luzonicum Gum Nonvolatiles.

The topical composition may further comprise a wide range of optional ingredients that do not deleteriously affect the composition's ability to stimulate AMP concentration on the surface or the composition's ability to regulate the balance of bacteria on the skin. The CTFA International Cosmetic Ingredient Dictionary and Handbook, Eleventh Edition 2005, and the 2004 CTFA International Buyer's Guide, both of which are incorporated by reference herein in their entirety, describe a wide variety of non- limiting cosmetic and pharmaceutical ingredients commonly used in the skin care industry, that are suitable for use in the compositions of the present invention. Examples of these functional classes include: abrasives, anti-acne agents, anti-caking agents, antioxidants, binders, biological additives, bulking agents, chelating agents, chemical additives; colorants, cosmetic astringents, cosmetic biocides, denaturants, drug astringents, emulsifiers, external analgesics, film formers, fragrance components, opacifying agents, plasticizers, preservatives (sometimes referred to as antimicrobials), propellants, reducing agents, skin bleaching agents, skin-conditioning agents (emollient, miscellaneous, and occlusive), skin protectants, solvents, surfactants, foam boosters, hydrotropes, solubilizing agents, suspending agents (nonsurfactant), sunscreen agents, ultraviolet light absorbers, detackifiers, and viscosity increasing agents (aqueous and nonaqueous). Examples of other functional classes of materials useful herein that are well known to one of ordinary skill in the art include solubilizing agents, sequestrants, keratolytics, topical active ingredients, and the like.

The topical compositions exhibit a pH in the range of from about 3 to about 12.0, or a pH in the range of from about 4 to about 8, or in the range of from about 4.5 and about 7. When necessary, a pH adjusting agent or constituent may be used to provide and/or maintain the pH of a composition. Exemplary pH adjusting agents include, but are not limited to, organic acids, such as citric acid, lactic acid, formic acid, acetic acid, proponic acid, butyric acid, caproic acid, oxalic acid, maleic acid, benzoic acid, carbonic acid, and the like.

The form of the composition of the present invention is not particularly limited. In one or more embodiments, topical compositions of the present invention may be formulated as a cleansing lotion, a foamable composition, a rinse-off soap cleansing composition, a thickened gel composition, or may be applied to a wipe.

In one or more embodiments, the topical composition is formulated as a foamable composition. One or more foam agents may optionally be included in the foamable composition.

Any foaming agent conventionally known and used may be employed in the topical composition. In one or more embodiments, the foam agent comprises a non-ionic foam agent such as decyl glucoside or an amphoteric foam agent such as cocamidopropylbetaine. In one or more embodiments, the amount of nonionic or amphoteric foam agent is from about 0.5 to about 3.5 wt. %, in other embodiments from about 1.0 to about 3.0 wt. %, based upon the total weight of the topical composition. In one or more embodiments, the amount of decyl glucoside or cocamidopropylbetaine is from about 0.5 to about 3.5 wt. %, in other embodiments from about 1.0 to about 3.0 wt. %, based upon the total weight of the topical composition.

In some exemplary embodiments, the foaming agents include one or more of silicone glycol and fluorosurfactants. Silicone glycols may be generally characterized by containing one or more Si-O-Si linkages in the polymer backbone. Silicone glycols include organopolysiloxane dimethicone polyols, silicone carbinol fluids, silicone polyethers, alkylmethyl siloxanes, amodimethicones, trisiloxane ethoxylates, dimethiconols, quaternized silicone glycols, polysilicones, silicone crosspolymers, and silicone waxes.

Examples of silicone glycols include dimethicone PEG-7 undecylenate, PEG-10 dimethicone, PEG-8 dimethicone, PEG-12 dimethicone, perfluorononylethyl carboxydecal PEG 10, PEG-20/PPG-23 dimethicone, PEG-11 methyl ether dimethicone, bis-PEG/PPG-20/20 dimethicone, silicone quats, PEG-9 dimethicone, PPG-12 dimethicone, fluoro PEG-8 dimethicone, PEG-23/PPG-6 dimethicone, PEG-20/PPG-23 dimethicone, PEG 17 dimethicone, PEG-5/PPG-3 methicone, bis-PEG-18 methyl ether dimethyl silane, bis-PEG-20 dimethicone, PEG/PPG-20/15 dimethicone copolyol and sulfosuccinate blends, PEG-8 dimethicone\dimmer acid blends, PEG-8 dimethicone\fatty acid blends, PEG-8 dimethicone\cold pressed vegetable oil\polyquaternium blends, random block polymers and mixtures thereof.

The amount of silicone glycol foam agent is not particularly limited, so long as an effective amount to produce foaming is present. In certain embodiments, the effective amount to produce foaming may vary, depending upon the amount of other ingredients that are present. In one or more embodiments, the composition includes at least about 0.002 wt. % of silicone glycol foam agent, based upon the total weight of the composition. In another embodiment, the composition includes at least about 0.01 wt. % of silicone glycol foam agent, based upon the total weight of the composition. In yet another embodiment, the composition includes at least about 0.05 wt. % of silicone glycol foam agent, based upon the total weight of the composition.

In some exemplary embodiments, the foam agent is present in an amount of from about 0.002 to about 4.0 wt. %, or in an amount of from about 0.01 to about 2.0 wt. %, based upon the total weight of the composition. It is envisioned that higher amounts may also be effective to produce foam. All such weights as they pertain to listed ingredients are based on the active level, and therefore, do not include carriers or by-products that may be included in commercially available materials, unless otherwise specified.

In other embodiments, it may be desirable to use higher amounts of foam agent. For example, in certain embodiments where the foaming composition of the present invention includes a cleansing product that is applied to a surface and then rinsed off, higher amounts of foam agent may be employed. In these embodiments, the amount of foam agent is present in amounts up to about 35.0 wt. %, based upon the total weight of the composition.

The topical composition of the present invention may be formulated as an aerosol or non-aerosol foamable composition. In some exemplary embodiments the topical composition is dispensed from an unpressurized or low-pressure dispenser which mixes the composition with air.

In one or more embodiments, the viscosity of the non-aerosol foamable composition is less than about 100 mPas, in one embodiment less than about 50 mPas, and in another embodiment less than about 25 mPas.

In one or more embodiments, the compositions of the present invention may be formulated as a lotion. As is known in the art, lotions include oil-in-water emulsions as well as water-in-oil emulsions, oil-water-oil, and water-oil-water. A wide variety of ingredients may be present in either the oil or water phase of the emulsion. That is, the lotion formulation is not particularly limited.

Compositions of the present invention may be characterized by reference to viscosity and/or rheological properties. In one or more embodiments, the viscosity may be expressed as a standard, single-point type viscosity, as measured on a Brookfield Digital viscometer at a temperature of about 20° C., using spindle T-D, heliopath, at a speed of 10 rpm. In one or more embodiments, the compositions may have a viscosity of from about 2000 to about 120,000 cPs.

In one or more embodiments, compositions of the present invention may be characterized as lotions, having a viscosity of less than about 120,000 centipoise (cPs), in other embodiments, less than about 100,000, and in other embodiments, less than about 75,000 cPs. In one or more embodiments, the lotion compositions may have a viscosity of from about 3000 to about 50,000 cPs, in other embodiments, from about 4000 to about 30,000 cPs.

Exemplary lotion formulations include those containing water and/or alcohols and emollients such as hydrocarbon oils and waxes, silicone oils, hyaluronic acid, vegetable, animal or marine fats or oils, glyceride derivatives, fatty acids or fatty acid esters or alcohols or alcohol ethers, lanolin and derivatives, polyhydric alcohols or esters, wax esters, sterols, phospholipids and the like, and generally also emulsifiers (nonionic, cationic or anionic), although some of the emollients inherently possess emulsifying properties.

In one or more embodiments, compositions of the present invention may be characterized as serum, having a viscosity of from about 2000 to about 3000 cPs.

In one or more embodiments, compositions of the present invention may be characterized as creams, having a viscosity of from about 30,000 to about 100,000 cPs, in other embodiments from about 50,000 to about 80,000 cPs.

In one or more embodiments, compositions according to the present invention are pourable at room temperature, i.e. a temperature in the range of from about 20 to about 25° C. In one or more embodiments, the lotion formulations are viscous enough to hold a shape or not flow for a desired period of time. In other embodiments, compositions of the present invention are creams or ointments, and are not pourable and do not flow at room temperature and will not conform to a container when placed into the container at room temperature.

In one or more embodiments, the topical composition of the present invention may include thickeners and optionally one or more stabilizers. Examples of thickeners and stabilizers include polyurethane-based thickeners, such as steareth-100/PEG-136/HDI copolymer (Rheoluxe® 811); sodium chloride; propylene glycol; PEG-120 methyl glucose dioleate and methyl gluceth-10 (Ritathix DOE, available from Rita Corp.); hydroxyethyl cellulose; quaternized hydroxyethyl cellulose (Polyquaternium-10); hydroxypropyl cellulose; methyl cellulose; carboxymethyl cellulose; and ammonium acryloyldimethyltaurate/VP copolymer.

In one or more exemplary embodiments, the topical composition may be thickened with polyacrylate thickeners such as those conventionally available and/or known in the art. Examples of polyacrylate thickeners include carbomers, acrylates/C10-30 alkyl acrylate cross-polymers, copolymers of acrylic acid and alkyl (C5-C10) acrylate, copolymers of acrylic acid and maleic anhydride, and mixtures thereof. In one or more embodiments, the gel composition includes an effective amount of a polymeric thickener to adjust the viscosity of the gel to a viscosity range of from about 1000 to about 65,000 centipoise. In one embodiment, the viscosity of the gel is from about 5000 to about 35,000, and in another embodiment, the viscosity is from about 10,000 to about 25,000. The viscosity is measured by a Brookfield RV Viscometer using RV and/or LV Spindles at 22° C.+/−3° C.

As will be appreciated by one of skill in the art, the effective amount of thickener will vary depending upon a number of factors, including the amount of other ingredients in the topical composition. In one or more embodiments, an effective amount of thickener is at least about 0.01 wt. %, based upon the total weight of the composition. In other embodiments, the effective amount is at least about 0.02 wt. %, or at least about 0.05 wt. %, or at least about 0.1 wt. %. In some exemplary embodiment, the effective amount of thickener is at least about 0.5 wt. %, or at least about 0.75 wt. %, based upon the total weight of the composition. In one or more embodiments, the compositions according to the present invention comprise up to about 10% by weight of the total composition of a polymeric thickener. In certain embodiments, the amount of thickener is from about 0.01 to about 1.0 wt. %, or from about 0.02 to about 0.4 wt. %, or from about 0.05 to about 0.3 wt. %, based upon the total weight of the composition. The amount of thickener may be from about 0.1 to about 10.0 wt. %, or from about 0.5 to about 5.0 wt. %, or from about 0.75 to about 2.0 wt. %, based upon the total weight of the composition.

In one or more embodiments, the topical composition may further comprise a neutralizing agent. Examples of neutralizing agents include amines, alkanolamines, alkanolamides, inorganic bases, amino acids, including salts, esters and acyl derivatives thereof. Exemplary neutralizing agents include triethanolamine, sodium hydroxide, monoethanolamine and dimethyl stearylamine. Other neutralizing agents are also known, such as $HO(C_mH_{2m})_2NH$, where m has the value of from 2 to 3, and aminomethyl propanol, aminomethyl propanediol, and ethoxylated amines, such as PEG-25 cocamine, polyoxyethylene (5) cocamine (PEG-5 cocamine), polyoxyethylene (25) cocamine (PEG-25 cocamine), polyoxyethylene (5) octadecylamine (PEG-5 stearamine), polyoxyethylene (25) octadecylamine (PEG-25 stearamine), polyoxyethylene (5) tallowamine (PEG-5 tallowamine), polyoxyethylene (15) oleylamine (PEG-15 oleylamine), polyethylene (5) soyamine (PEG-5 soyamine), and polyoxyethylene (25) soyamine (PEG-15 soyamine). A number of these are commercially available under the trade name of Ethomeen® from Akzo Chemie America, Armak Chemicals of Chicago, Ill.

In some exemplary embodiments the neutralizing agent includes at least one of sodium hydroxide or sodium hydroxide precursors. Solutions of sodium hydroxide in water are non-limiting examples of neutralizers containing sodium hydroxide.

The neutralizing agent is employed in an effective amount to neutralize a portion of the carboxyl groups of the thickening agent, and produce the desired pH range. The pH of un-neutralized thickening agent dispersed in water is generally acidic. For example, the pH of Carbopol® polymer dispersions is approximately in the range of 2.5 to 3.5, depending upon the polymer concentration. An effective amount of neutralizing agent, when added to the thickener dispersion, adjusts the pH to a desired range of about 4.1 to 4.8, or of about 4.2 to 4.6. The amount of neutralizing agent necessary to effect this pH range will vary depending upon factors such as the type of thickening agent, the amount of thickening agent, etc. However, in general, amounts less than 1.0 wt. % or ranging from about 0.001 to about 0.3 wt. % by weight of the neutralizing agent are considered sufficient and effective.

In some exemplary embodiments the topical composition can also be formulated as a cleansing composition or soap. A fatty acid or a fatty acid ester may be used in conjunction with an alkali or base from the water phase to form a soap which has good water solubility as well as oil solubility properties and hence, is an excellent emulsifier. The soap, as explained above, can be in the form of a lotion soap, a foam soap, or any other common form known to one of skill in the art. Typical commercial blends such as oleic fatty acid, coconut fatty acid, soya fatty acid and tall oil fatty acid can be used. Preferably, the fatty acid comprises from about 5.0 to about 10.0 wt. % of the total topical composition.

As explained above, a base may be utilized in conjunction with the fatty acid to produce a soap on an equivalent basis of from about 2.7 to 0.8 equivalents to 1 equivalent of base. Examples of suitable base include organic alkalis or amines such as monoethanolamine, triethanolamine, and mixed isopropanolamines such as diisopropanolamine. Examples of suitable base also include inorganic alkalis, such as potassium hydroxide, sodium hydroxide, ammonium hydroxide, soda ash, and ammonia.

In addition, one or more surfactants can be included in the oil phase of the cleaning composition in amounts preferably ranging up to about 25.0 wt. %. A surfactant is generally any substance which reduces the surface tension of a liquid. They break down the interface between water and oils/dirt. By holding the oils/dirt in suspension, they can be easily removed from the surface (i.e. skin).

In some exemplary embodiments, the surfactant includes a mixture of primary and secondary surfactants. Nonionic surfactants, i.e., surfactants which are uncharged (neutral) and without cationic or anionic sites, are preferred since they tend to render the composition stable, i.e., impart two desirable properties thereto. The first property is that of a suitable long shelf life. In other words, the emulsion can be held together at room temperature for long periods of time. The second desirable property is that upon use of the cleaning composition, the surfactant permits breakage of the emulsion or opening up thereof such that the hydrocarbon oil is readily released. The surfactant can also be an anionic surfactant, which carry a negative charge and are ionized in solution. The surfactant can also be a cationic surfactant, which carry a positive charge and ionize in solution. The surfactant can also be an amphoteric surfactant, which have the ability to be anionic (negatively charged), cationic (positively charged), or nonionic (uncharged, neutral) in solution depending on the pH.

It will be appreciated by one skilled in the art that in one or more embodiments, surfactant and/or surfactant combinations may be chosen to limit irritation of the composition and/or to enhance the effect of the active ingredient. In yet another embodiment, surfactant and/or surfactant combinations may be chosen to allow maximum bioavailability of the active ingredient. Non-limiting exemplary examples of surfactant combinations, levels of which will be known to one skilled in the art, are sodium lauryl ether sulfate (SLES) and/or cocamidopropyl betaine and/or disodium cocoamphodiacetate and/or surfactants of similar structure.

Non-limiting exemplary examples of surfactants that are envisioned in the present composition include betaines such as cocamidoproyl betaine; sulfonates and sulfates such as sodium laureth sulfate, sodium cocosulfate, sodium trideceth sulfate, and alkylbenzene sulfonate; glucosides, such as lauryl gluocoside and decyl glucoside; sodium cocoyl isothionate, sodium cocoyl glycinate, cocamidopropyl hydroxysultaine, PEG-80 sorbitan laurate, di-alkyl sulfosuccinate, lignosulfonates, disodium cocoamphodiacetate, lauryl glucoside, and PEG-80 sodium laurate.

In some exemplary embodiments, the topical cleansing composition comprises at least one primary surfactant and at least one secondary surfactant. A primary surfactant may include, for example, sodium laureth sulfate. Exemplary secondary surfactants may include, for example, one or more of cocamidopropyl betaine, disodium cocoamphodiacetate, cocamidopropyl hydroxysultaine, and lauryl glucoside.

As will be appreciated by one of skill in the art, the amount of surfactant will vary depending upon a number of factors, including the amount of other ingredients in the topical composition. In some exemplary embodiments, the surfactant is included in at least about 0.5 wt. %, or at least about 0.75 wt. %, or at least about 1.0 wt. %, or at least about 2.0 wt. %, based upon the total weight of the composition. In one or more exemplary embodiments, the compositions according to the present invention comprise up to about 25 wt. %, or up to about 18 wt. %, or up to about 15 wt. %, or up to about 12 wt. %, or up to about 9.0 wt. % of the total composition of one or more surfactant. In certain exemplary embodiments, the amount of surfactant is from about 2.0 wt. % to about 20 wt. %, or from about 2.5 wt. % to about 18. wt. %, or from about 3.0 wt. % to about 13.0 wt. %, based upon the total weight of the composition.

The composition of the present invention may be employed in any type of dispenser typically used for gel products, for example pump dispensers. A wide variety of pump dispensers are suitable. Pump dispensers may be affixed to bottles or other free-standing containers. Pump dispensers may be incorporated into wall-mounted dispensers. Pump dispensers may be activated manually by hand or foot pump, or may be automatically activated. Useful dispensers include those available from GOJO Industries under the designations NXT® and TFX™ as well as traditional bag-in-box dispensers. Examples of dispensers are described in U.S. Pat. Nos. 5,265,772, 5,944,227, 6,877,642, 7,028,861, 7,611,030, and 7,621,426, all of which are incorporated herein by reference. In one or more embodiments, the dispenser includes an outlet such as a nozzle, through which the composition is dispensed. In some exemplary embodiments, the topical composition is used in dispensers that employ foaming pumps, which combine ambient air or an inert gas and the composition in a mixing chamber and pass the mixture through a mesh screen.

In one or more embodiments, the topical composition is integrated into wipe composition. Wipe compositions in accordance with this invention include at least one alcohol, a $C_{1-10}$ alkanediol enhancer, and are applied to a wipe substrate. In some exemplary embodiments, the wipe composition is alcohol-free.

Wipe substrates used in antimicrobial wipes are further described in U.S. Pat. Nos. 5,686,088, 6,410,499, 6,436,892, 6,495,508, 6,844,308. In one or more embodiments, the wipe may comprise a laminate formed by spunbonding/meltblowing/spunbonding (SMS). Generally, an SMS material contains a meltblown web sandwiched between two exteriors spunbond webs. SMS materials are further described in U.S. Pat. Nos. 4,041,203, 5,169,706, 5,464,688, and 4,766,029, and are commercially available, for example from Kimberly-Clark Corporation under marks such as Spunguard 7 and Evolution 7. The SMS laminate may be treated or untreated.

In some exemplary embodiments, the topical composition increases the presence of AMPs on the skin, including at least human beta defensin (HBD) 1, HBD-2, and HBD-3 as well as LL-37.

In some exemplary embodiments, a topical composition comprising up to about 10.0 wt. % of a polypeptide active ingredient increases the concentration of HBD-1 by a statistically significant amount, as compared to an otherwise identical composition that does not include the active ingredient. In some exemplary embodiments, a topical composition comprising up to about 10.0 wt. % of a polypeptide active ingredient increases the concentration of HBD-1 by at least 25%, or at least 100%, or at least 500%, or at least 800%, or at least 1000%, as compared to an otherwise identical composition that does not include the active ingredient. In some exemplary embodiments, a topical composition comprising up to about 10.0 wt. % of a polypeptide active ingredient increases the concentration of HBD-1 by at least 1,400%, or by at least 1,700%, as compared to an otherwise identical composition that does not include the active ingredient.

In some exemplary embodiments, a topical composition comprising up to about 10.0 wt. % of a polypeptide active ingredient increases the concentration of HBD-2 by a statistically significant amount, as compared to an otherwise identical composition that does not include the active ingredient. In some exemplary embodiments, a topical composition comprising up to about 10.0 wt. % of a polypeptide active ingredient increases the concentration of HBD-2 by at least 25%, or at least 100%, or at least 500%, or at least 800%, or at least 1000%, as compared to an otherwise identical composition that does not include the active ingredient. In some exemplary embodiments, a topical composition comprising up to about 10.0 wt. % of a polypeptide active ingredient increases the concentration of HBD-2 by at least 1,100%, or by at least 1,200%, or by at least 2,000%, as compared to an otherwise identical composition that does not include the active ingredient.

In some exemplary embodiments, a topical composition comprising up to about 10.0 wt. % of a polypeptide active ingredient increases the concentration of HBD-3 by a statistically significant amount, as compared to an otherwise identical composition that does not include the active ingredient. In some exemplary embodiments, a topical composition comprising up to about 10.0 wt. % of a polypeptide active ingredient increases the concentration of HBD-3 by at least 25%, or at least 50%, or at least 100%, or at least 500%, or at least 800%, or at least 1000%, as compared to an otherwise identical composition that does not include the active ingredient. In some exemplary embodiments, a topical composition comprising up to about 10.0 wt. % of a polypeptide active ingredient increases the concentration of HBD-3 by at least 2,000%, or by at least 2,500%, or by at least 4,000%, as compared to an otherwise identical composition that does not include the active ingredient.

In some exemplary embodiments, a topical composition comprising up to about 10.0 wt. % of a natural extract active ingredient increases the concentration of HBD-1 by a statistically significant amount, as compared to an otherwise identical composition that does not include the active ingredient. Particularly, a topical composition comprising up to about 10.0 wt. % linseed extract increases the concentration of HBD-1 by at least 10%, or at least 20%, or at least 50%, or at least 75%, or at least 95%, as compared to an otherwise identical composition that does not include the active ingredient.

In some exemplary embodiments, a topical composition comprising up to about 10.0 wt. % of a natural extract active ingredient increases the concentration of HBD-2 by a statistically significant amount, as compared to an otherwise identical composition that does not include the active ingredient. Particularly, a topical composition comprising up to about 10.0 wt. % linseed extract increases the concentration of HBD-2 by at least 5%, or at least 10%, or at least 20%, or at least 23%, as compared to an otherwise identical composition that does not include the active ingredient In some exemplary embodiments, a topical composition comprising up to about 10.0 wt. % of a natural extract active ingredient increases the concentration of HBD-3 by a statistically significant amount, as compared to an otherwise identical composition that does not include the active ingredient. Particularly, a topical composition comprising up to about 10.0 wt. % linseed extract increases the concentration of HBD-3 by at least 5%, or at least 10%, or at least 20%, or at least 29%, as compared to an otherwise identical composition that does not include the active ingredient.

In some exemplary embodiments, a topical composition comprising up to about 10.0 wt. % of a natural extract active ingredient increases the concentration of LL-37 by a statistically significant amount, as compared to an otherwise identical composition that does not include the active ingredient. Particularly, a topical composition comprising up to about 10.0 wt. % linseed extract increases the concentration of LL-37 by at least 5%, or at least 10%, or at least 20%, or at least 30%, or at least 38%, as compared to an otherwise identical composition that does not include the active ingredient.

In some exemplary embodiments, a topical composition comprising up to about 10.0 wt. % of a natural extract active ingredient decreases the concentration of IL-8 by a statistically significant amount, as compared to an otherwise identical composition that does not include the active ingredient. Particularly, a topical composition comprising up to about 10.0 wt. % linseed extract decreases the concentration of IL-8 by at least 5%, or at least 10%, or at least 20%, or at least 30%, or at least 33%, as compared to an otherwise identical composition that does not include the active ingredient.

In some exemplary embodiments, a topical composition comprising up to about 10.0 wt. % of a natural extract active ingredient in a rinse-off formulation increases the concentration of HBD-1 by a statistically significant amount, as compared to an otherwise identical composition that does not include the active ingredient. Particularly, a topical composition comprising up to about 10.0 wt. % linseed extract in a rinse-off formulation increases the concentration of HBD-1 by at least 1 ng/mL, or at least 4 ng/mL, or at least 6 ng/mL, or at least 10 ng/mL, or at least 16 ng/mL, as compared to an otherwise identical composition that does not include the active ingredient.

In some exemplary embodiments, a topical composition comprising up to about 10.0 wt. % of a natural extract active ingredient in a rinse-off formulation increases the concentration of HBD-2 by a statistically significant amount, as compared to an otherwise identical composition that does not include the active ingredient. Particularly, a topical composition comprising up to about 10.0 wt. % linseed extract in a rinse off formulation increases the concentration of HBD-2 by at least 1 ng/mL, or at least 10 ng/mL, or at least 25 ng/mL, or at least 40 ng/mL, or at least 60 ng/mL, as compared to an otherwise identical composition that does not include the active ingredient.

In some exemplary embodiments, a topical composition comprising up to about 10.0 wt. % of a natural extract active ingredient in a rinse-off formulation increases the concentration of HBD-3 by a statistically significant amount, as compared to an otherwise identical composition that does not include the active ingredient. Particularly, a topical composition comprising up to about 10.0 wt. % linseed extract in a rinse-off formulation increases the concentration of HBD-3 by at least 1 ng/mL, or at least 50 ng/mL, or at least 100 ng/mL, or at least 150 ng/mL, or at least 185 ng/mL, as compared to an otherwise identical composition that does not include the active ingredient.

EXAMPLES

The following examples are included for purposes of illustration and are not intended to limit the scope of the methods described herein.

EXAMPLE 1

To determine the optimal dose of active ingredient, test dose response studies were run using both Decorinyl® and Pamitoyl Pentapeptided-3. These test dose response studies were commissioned to determine the concentration of HBD-1 at various levels of the active ingredients. Neonatal Human Epidermal Keratinocytes (NHEK; Life Technology, Grand Island, N.Y., USA) were cultured with keratinocyte growth medium (KGM, Medium 154: M-154-500 Life Technology with supplements S-001, Life Technologies). NHEK were seeded into 96-well plates at a density of 10000 cells in 200 µl medium per well. After 48 hours, the cells were incubated with varying concentrations of each ingredient solution in a culture medium (KGM) overnight (16 hours) at 37° C., 5% $CO_2$ and 95% humidity at four replicates for each concentration. Each of these active ingredients was tested at the following weight percents based on the weight of the total culture: 0.02 wt. %, 0.05 wt. %, 0.1 wt. %, 0.2 wt. %, 0.5 wt. %, 1.0 wt. %, 2.0 wt. %. Each of these compositions was compared to a control culture medium.

HBD-1 was detected using HBD-1 ELISA (enzyme-linked immunosorbent assay) developing kits (commercially available from Peprotech). ELISA were performed according to the manufactory instructions of each kit by adding 100 µl well of culture medium after overnight treatment. The substrate of ELISA reaction was using the substrate reagent from R&D Systems (DY999), and the reactions were stopped by adding 50 µl of 1N $H_2SO_4$ in each well. The results were measured using a colorimeter, absorbance was measured at 450 nanometers (nm) within 30 minutes. Wavelength correction was set to 570 nm. The concentration of each sample was calculated using ELISA standard curve.

The results are listed below in Table 1 and depicted graphically in FIG. 1. As illustrated below, a 1.0 and 2.0 wt. % concentration of Decorinyl® demonstrated an increase in HBD-1 concentration of 1763% and 1465% were observed for 1.0 wt. % and 2.0 wt. % Decorinyl®, respectively. Increases in HBD-1 concentration of 311% and 1561% were observed for 1.0 wt. % and 2.0 wt. % Pamitoyl Pentapeptided-3, respectively.

TABLE 1

| Active Ingredient | wt. % | HBD-1 (pg/ml) |
|---|---|---|
| Control | Medium | 63 |
| Decorinyl ® | 2% | 986 |
|  | 1% | 1174 |
|  | 0.5% | 130 |
|  | 0.2% | 107 |
|  | 0.1% | 138 |
|  | 0.05% | 84 |
|  | 0.02% | 67 |
| Pamitoyl Pentapeptided-3 | 2% | 1047 |
|  | 1% | 259 |
|  | 0.50% | 162 |
|  | 0.20% | 85 |
|  | 0.10% | 64 |
|  | 0.05% | 57 |
|  | 0.02% | 59 |

EXAMPLE 2

To determine the optimal dose of active ingredient, test dose response studies were run using both Decorinyl® and Pamitoyl Pentapeptided-3. These test dose response studies were commissioned to determine the concentration of HBD-2 at various levels of the active ingredients. Neonatal Human Epidermal Keratinocytes (NHEK; Life Technology, Grand Island, N.Y., USA) were cultured with keratinocyte growth medium (KGM, Medium 154: M-154-500 Life Technology with supplements S-001, Life Technologies). NHEK were seeded into 96-well plates at a density of 10000 cells in 200 µl medium per well. After 48 hours, the cells were incubated with varying concentrations of each ingredient solution in a culture medium (KGM) overnight (16 hours) at 37° C., 5% $CO_2$ and 95% humidity at four replicates for each concentration. Each of these active ingredients was tested at the following weight percents based on the weight of the total culture: 0.02 wt. %, 0.05 wt. %, 0.1 wt. %, 0.2 wt. %, 0.5 wt. %, 1.0 wt. %, 2.0 wt. %. Each of these compositions was compared to a control culture medium.

HBD-2 was detected using HBD-2 ELISA developing kits (commercially available from Peprotech). ELISA were performed according to the manufactory instructions of each kit by adding 100 µl well of culture medium after overnight treatment. The substrate of ELISA reaction was using the substrate reagent from R&D Systems (DY999), and the reactions were stopped by adding 50 µl of 1N $H_2SO_4$ in each well. The results were measured using a colorimeter, absorbance was measured at 450 nanometers (nm) within 30 minutes. Wavelength correction was set to 570 nm. The concentration of each sample was calculated using ELISA standard curve.

Figure 2:
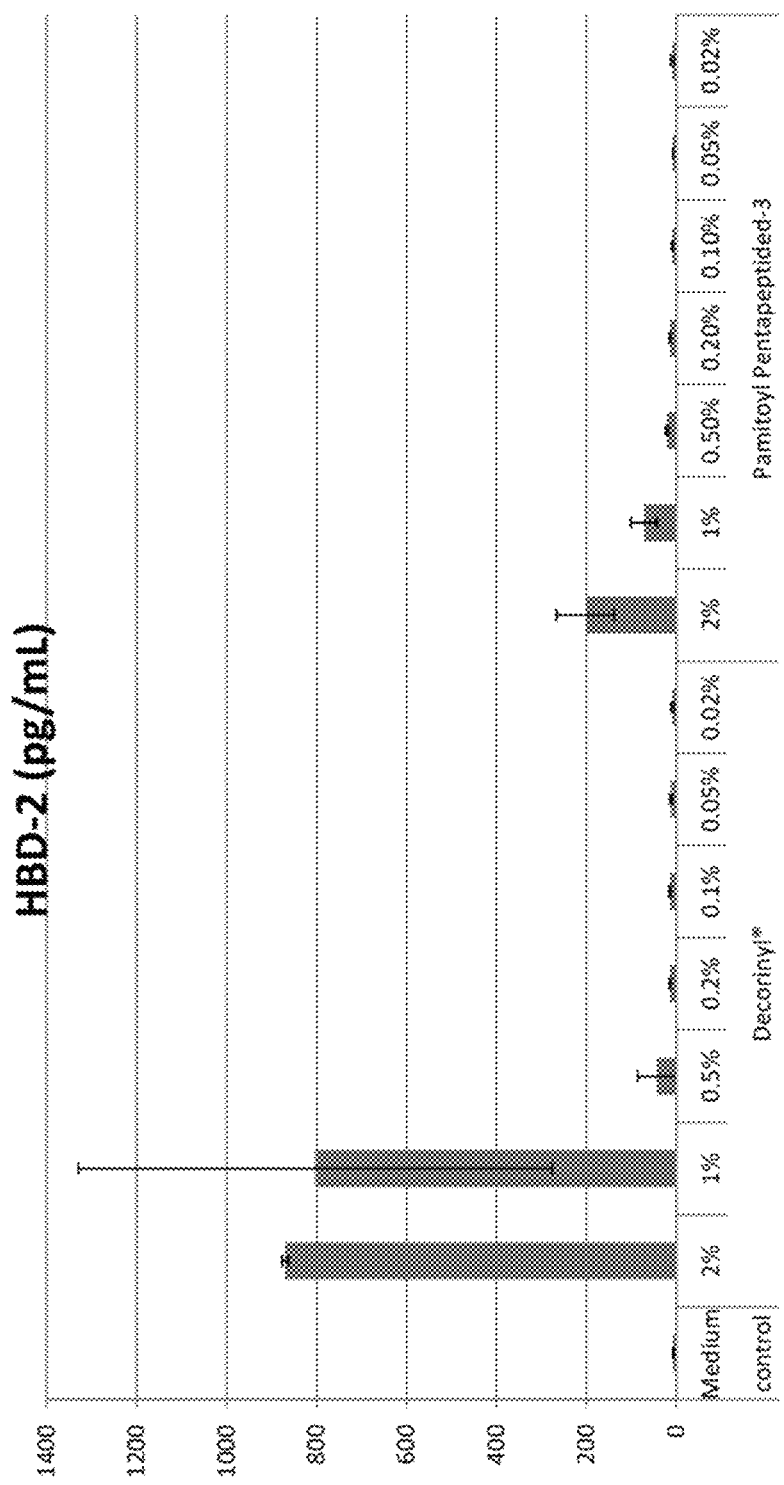
FIG. 2 graphically illustrates HBD-2 concentrations after treatment with various concentrations of Decorinyl and Pamitoyl Pentapeptide-3.

The results are listed below in Table 2 and depicted graphically in FIG. 2. Increases in HBD-2 concentration of 11,371% and 12,329% were observed for 1.0 wt. % and 2.0 wt. % Decorinyl® respectively. An increase in HBD-2 concentration of 2800% was observed for 2.0 wt. % Pamitoyl Pentapeptided-3.

TABLE 2

| Active Ingredient | wt. % | HBD-2 (pg/ml) |
|---|---|---|
| Control | Medium | 7 |
| Decorinyl ® | 2% | 870 |
|  | 1% | 803 |
|  | 0.5% | 44 |

TABLE 2-continued

| Active Ingredient | wt. % | HBD-2 (pg/ml) |
|---|---|---|
|  | 0.2% | 15 |
|  | 0.1% | 15 |
|  | 0.05% | 12 |
|  | 0.02% | 9 |
| Pamitoyl Pentapeptided-3 | 2% | 203 |
|  | 1% | 72 |
|  | 0.50% | 21 |
|  | 0.20% | 14 |
|  | 0.10% | 9 |
|  | 0.05% | 8 |
|  | 0.02% | 9 |

EXAMPLE 3

To determine the optimal dose of active ingredient, test dose response studies were run using both Decorinyl® and Pamitoyl Pentapeptided-3. These test dose response studies were commissioned to determine the concentration of HBD-3 at various levels of the active ingredients. Neonatal Human Epidermal Keratinocytes (NHEK; Life Technology, Grand Island, N.Y., USA) were cultured with keratinocyte growth medium (KGM, Medium 154: M-154-500 Life Technology with supplements S-001, Life Technologies). NHEK were seeded into 96-well plates at a density of 10000 cells in 200 µl medium per well. After 48 hours, the cells were incubated with varying concentrations of each ingredient solution in a culture medium (KGM) overnight (16 hours) at 37° C., 5% $CO_2$ and 95% humidity at four replicates for each concentration. Each of these active ingredients was tested at the following weight percents based on the weight of the total culture: 0.02 wt. %, 0.05 wt. %, 0.1 wt. %, 0.2 wt. %, 0.5 wt. %, 1.0 wt. %, 2.0 wt. %. Each of these compositions was compared to a control culture medium.

HBD-3 was detected using HBD-3 ELISA developing kits (commercially available from Peprotech). ELISA were performed according to the manufactory instructions of each kit by adding 100 µl/well of culture medium after overnight treatment. The substrate of ELISA reaction was using the substrate reagent from R&D Systems (DY999), and the reactions were stopped by adding 50 µl of 1N $H_2SO_4$ in each well. The results were measured using a colorimeter, absorbance was measured at 450 nanometers (nm) within 30 minutes. Wavelength correction was set to 570 nm. The concentration of each sample was calculated using ELISA standard curve.

Figure 3:
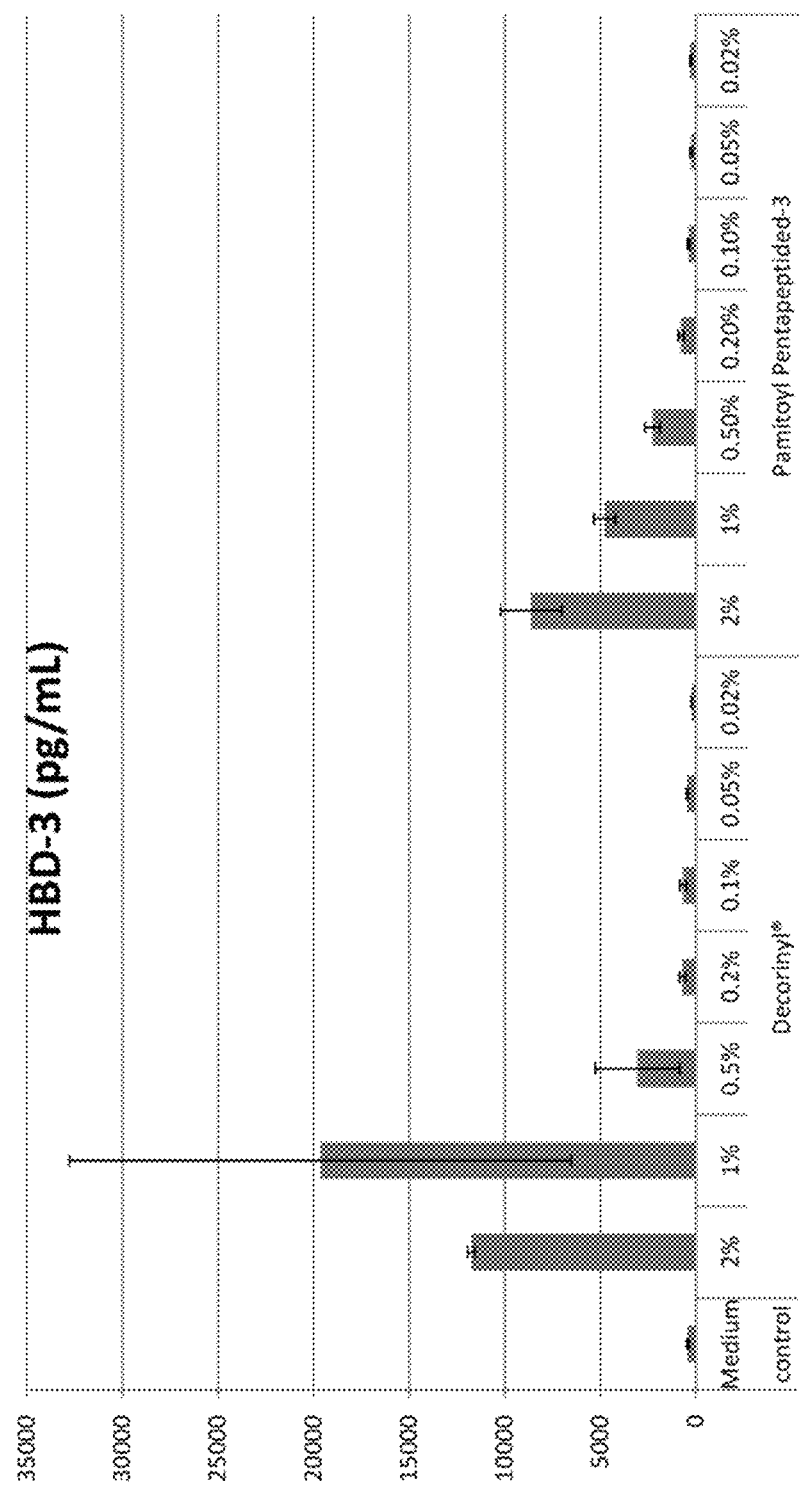
FIG. 3 graphically illustrates HBD-3 concentrations after treatment with various concentrations of Decorinyl and Pamitoyl Pentapeptide-3.

The results are shown below in Table 3 and depicted graphically in FIG. 3. Increases in HBD-3 concentration of 4438% and 2616% were observed for 1.0 wt. % and 2.0 wt. % Decorinyl® respectively. Increases in HBD-3 concentration of 1005% and 1890% were observed for 1.0 wt. % and 2.0 wt. % Pamitoyl Pentapeptided-3, respectively.

TABLE 3

| Active Ingredient | wt. % | HBD-3 (pg/ml) |
|---|---|---|
| Control | Medium | 433 |
| Decorinyl ® | 2% | 11759 |
|  | 1% | 19652 |
|  | 0.5% | 3058 |
|  | 0.2% | 703 |
|  | 0.1% | 682 |
|  | 0.05% | 456 |
|  | 0.02% | 226 |

TABLE 3-continued

| Active Ingredient | wt. % | HBD-3 (pg/ml) |
|---|---|---|
| Pamitoyl Pentapeptided-3 | 2% | 8617 |
|  | 1% | 4783 |
|  | 0.50% | 2278 |
|  | 0.20% | 775 |
|  | 0.10% | 387 |
|  | 0.05% | 242 |
|  | 0.02% | 288 |

EXAMPLE 4

Lipigenine™ was tested for its ability to stimulate an increase in HBD-1 concentration. The HBD-1 standard ABTS (2,2'-Azinobis [3-ethylbenzothiazoline-6-sulfonic acid]-diammonium salt) ELISA development kits were obtained from PeproTech (Cat# 900-K202). ELISA were performed according to the manufactory instructions of each kit by adding 100 µl/well of culture medium after overnight treatment. The substrate of ELISA reaction was using the substrate reagent from R&D Systems (DY999), and the reactions were stopped by adding 50 µl of 1N $H_2SO_4$ in each well. The Lipigenine™ culture was compared to the control medium which contained no other ingredients. The results were measured using a colorimeter, absorbance was measured at 450 nanometers (nm) within 30 minutes. Wavelength correction was set to 570 nm. The concentration of each sample was calculated using ELISA standard curve.

Figure 4:
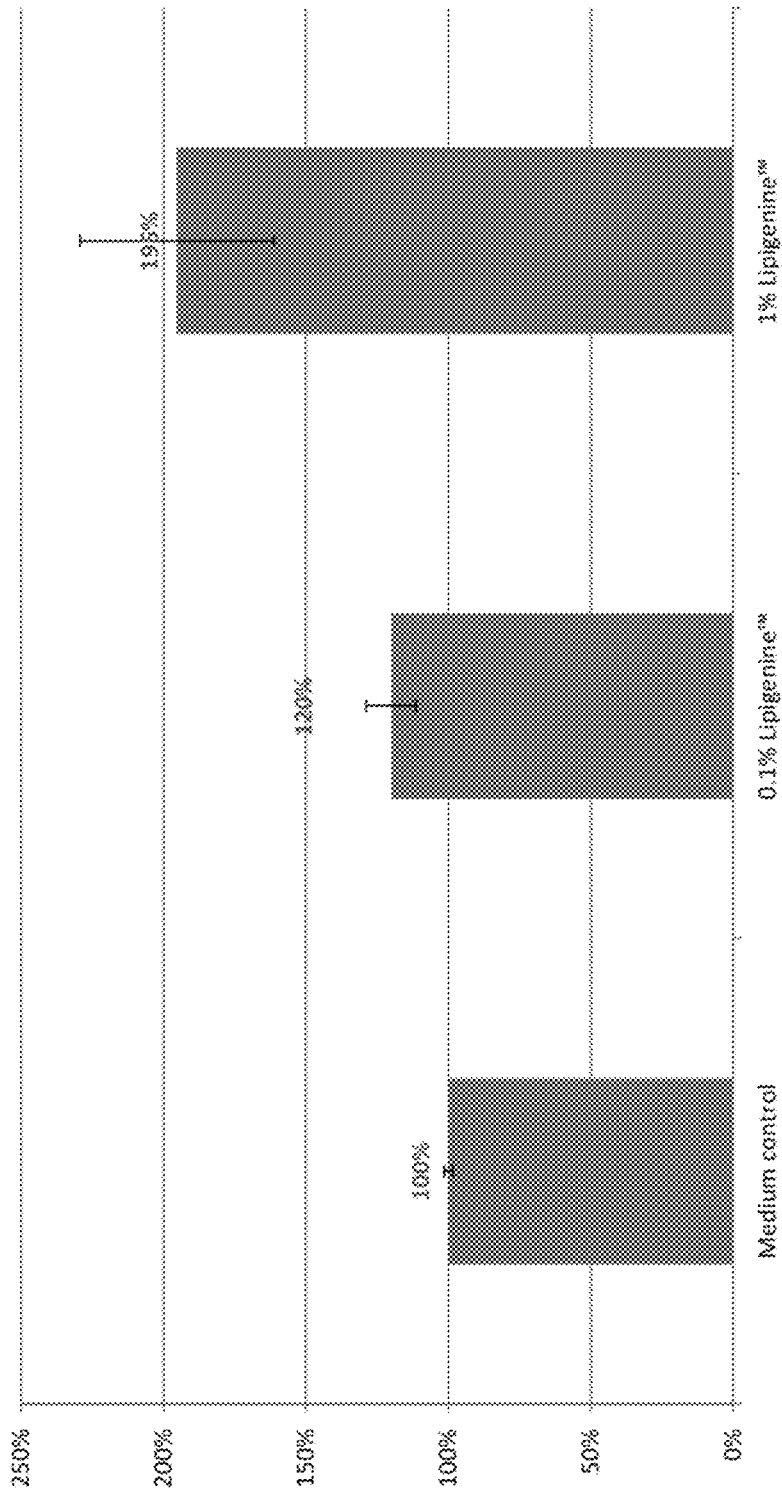
FIG. 4 graphically illustrates HBD-1 concentrations after treatment with 0.1% and 1.0% Lipigenine™.

The addition of Lipigenine™ showed high HBD-1 concentration at both 0.1% and 1% Lipigenine™ in solution as compared to the control. An increase in HBD-1 concentration of 20% was observed for 0.1% Lipigenine™ while an increase in HBD-1 concentration of 95% was observed for 1% Lipigenine™. These results are shown in FIG. 4.

EXAMPLE 5

Figure 5:
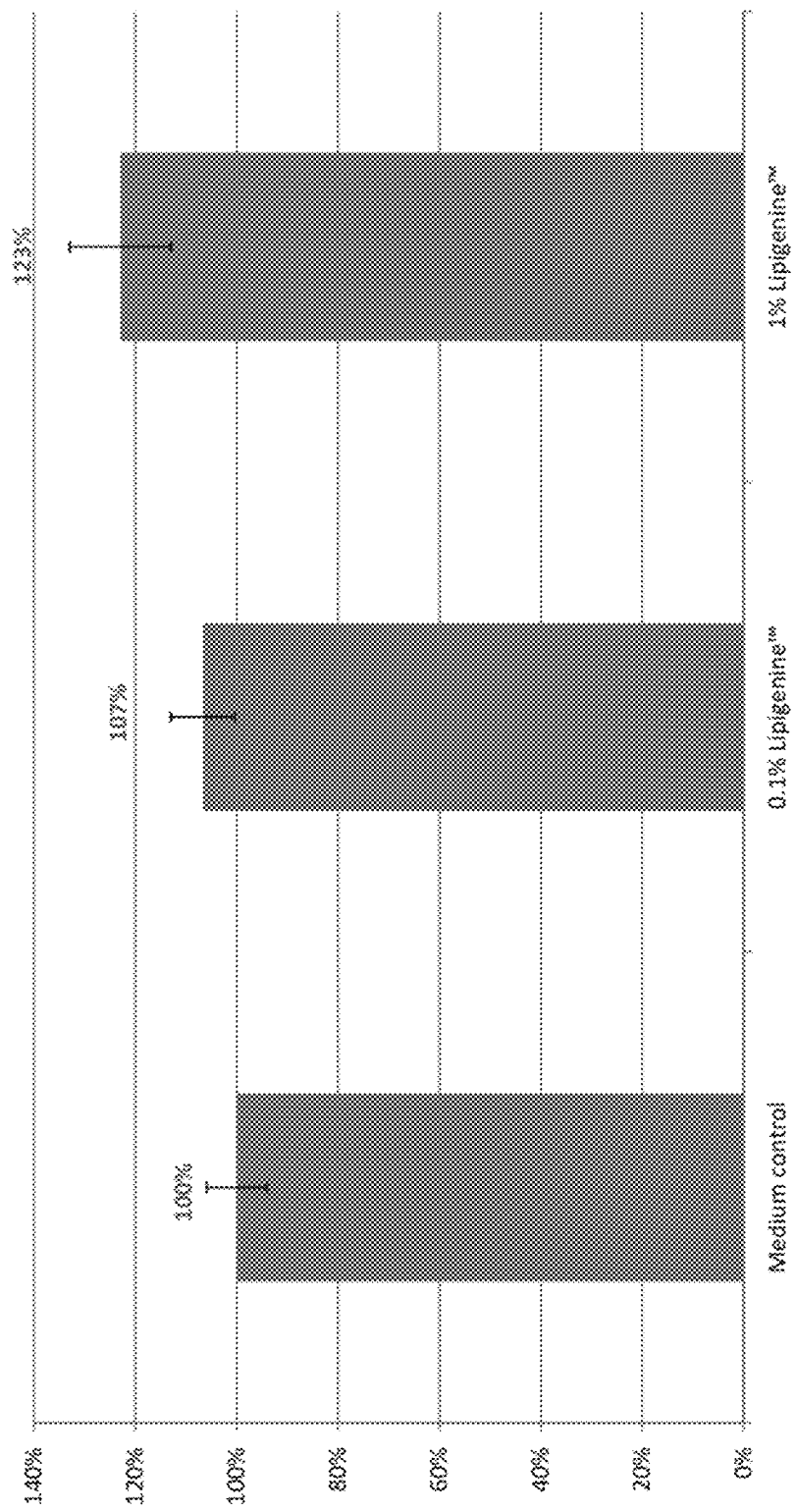
FIG. 5 graphically illustrates HBD-2 concentrations after treatment with 0.1% and 1.0% Lipigenine™.

Lipigenine™ was tested for its ability to stimulate an increase in HBD-2 concentration. The HBD-2 standard ABTS ELISA development kits were obtained from PeproTech (Cat# 900-K172). ELISA was performed according to the manufactory instructions of each kit by adding 100 µl/well of culture medium after overnight treatment. The substrate of ELISA reaction was using the substrate reagent from R&D Systems (DY999), and the reactions were stopped by adding 50 µl of 1N $H_2SO_4$ in each well. The Lipigenine™ culture was compared to the control medium which contained no other ingredients. The results were measured using a colorimeter, absorbance was measured at 450 nanometers (nm) within 30 minutes. Wavelength correction was set to 570 nm. The concentration of each sample was calculated using ELISA standard curve. [000126] The addition of Lipigenine™ showed increased HBD-2 concentrations at both 0.1% and 1% Lipigenine™ in solution as compared to the control. An increase in HBD-2 concentration of 7% was observed for a 0.1% Lipigenine™ formulation while an increase in HBD-2 expression of 23% was observed for a 1% Lipigenine™ formulation. These results are shown in FIG. 5.

EXAMPLE 6

Lipigenine™ was tested for its ability to stimulate an increase in HBD-3 concentration. The HBD-3 standard ABTS ELISA development kit was obtained from Pepro- Tech (Cat# 900-K210). ELISA were performed according to the manufactory instructions of each kit by adding 100 μl/well of culture medium after overnight treatment. The substrate of ELISA reaction was using the substrate reagent from R&D Systems (DY999), and the reactions were stopped by adding 50 μl of 1N $H_2SO_4$ in each well. The Lipigenine™ culture was compared to the control medium which contained no other ingredients. The results were measured using a colorimeter, absorbance was measured at 450 nanometers (nm) within 30 minutes. Wavelength correction was set to 570 nm. The concentration of each sample was calculated using ELISA standard curve.

Figure 6:
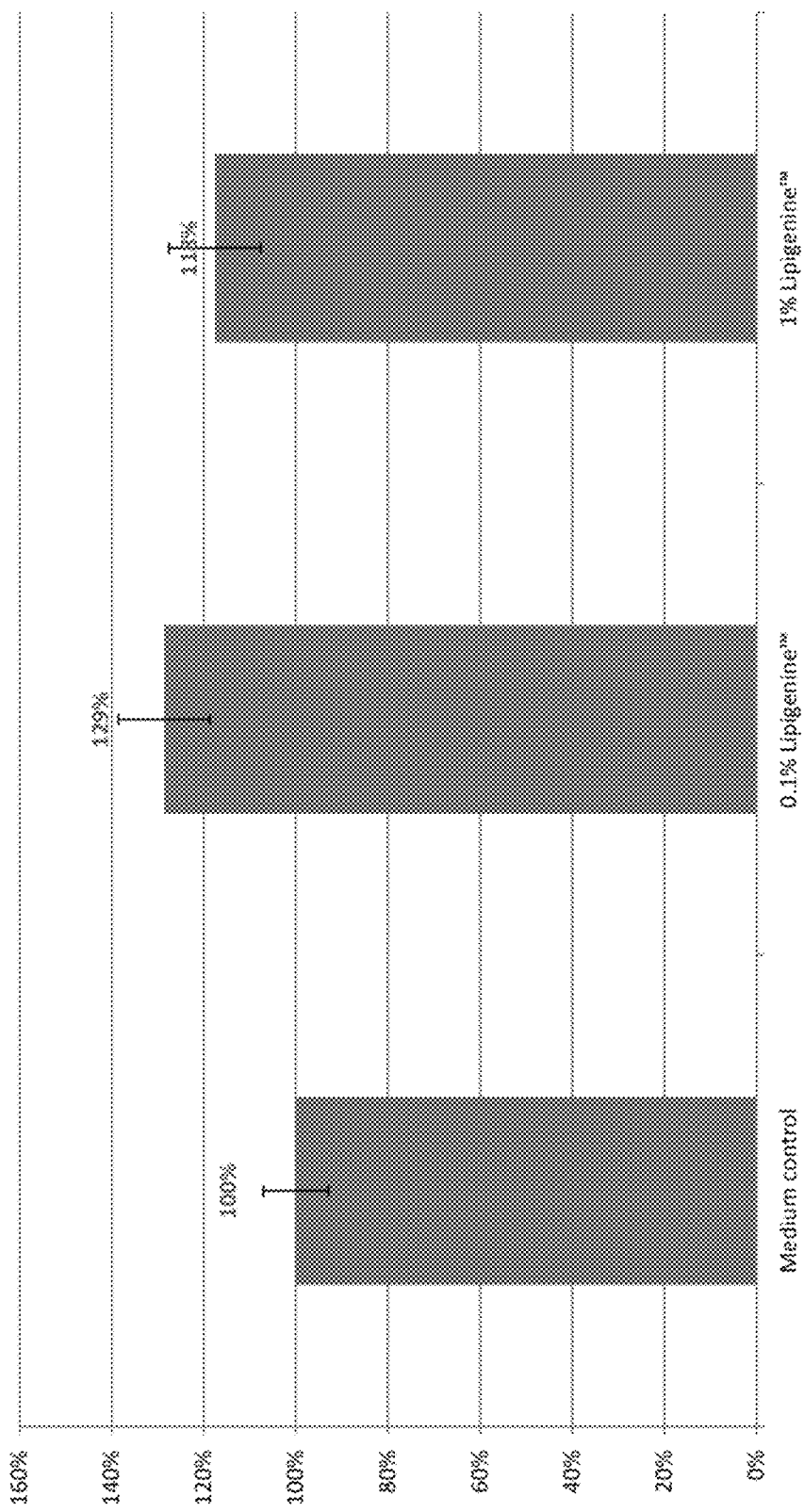
FIG. 6 graphically illustrates HBD-3 concentrations after treatment with 0.1% and 1.0% Lipigenine™.

The addition of Lipigenine™ showed increased HBD-3 concentration at both 0.1% and 1% Lipigenine™ in solution as compared to the control. An increase in HBD-3 concentration of 29% was observed for a 0.1% Lipigenine™ formulation while an increase in HBD-3 concentration of 18% was observed for a 1% Lipigenine™ formulation. These results are shown in FIG. 6.

EXAMPLE 7

A topical composition with Lipigenine™ was tested for its ability to increase concentration of Cathelicidin (LL37), an amphipathic alpha-helical peptide that plays an important role in defense against local infection and invasion of pathogens at sites of inflammation and wounds. The human LL-37 ELISA kit was obtained from Hycult Biotech (Cat#HK321). ELISA were performed according to the manufactory instructions of each kit by adding 100 μl/well of culture medium after overnight treatment. The results were measured using a colorimeter, absorbance was measured at 450 nanometers (nm) within 30 minutes. Wavelength correction was set to 570 nm.

Figure 7:
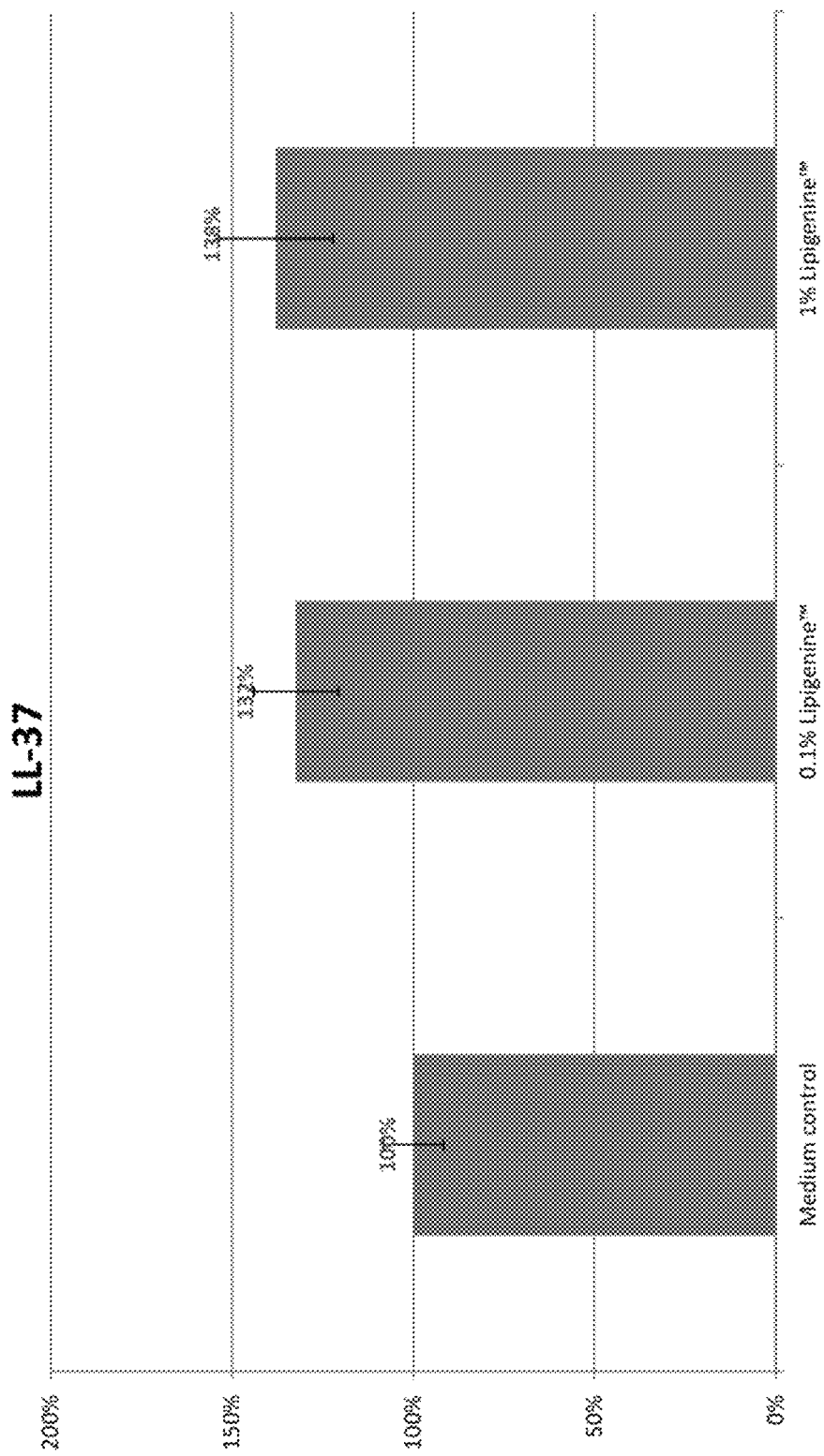
FIG. 7 graphically illustrates LL-37 concentrations after treatment with 0.1% and 1.0% Lipigenine™.

The addition of Lipigenine™ showed increased LL-37 concentration at both 0.1% and 1% Lipigenine™ in solution as compared to the control. An increase in LL-37 concentration of 32% for a 0.1% Lipigenine™ formulation while an increase in LL-37 concentration of 38% was observed for a 1% Lipigenine™ formulation. These results are shown in FIG. 7.

EXAMPLE 8

A topical composition with Lipigenine™ was tested for its ability to decrease concentration of Interleukin 8 (IL-8 or CXCL8) which is a chemokine and proinflammatory cytokine produced by macrophages and other cell types such as epithelial cells. It is secreted from keratinocytes in skin in response to inflammatory stimuli. IL-8 is secreted and is an important mediator of the immune reaction in the innate immune system response. IL-8 over-expressed is a biomarker of skin irritation. IL-8 is associated with inflammation and plays a role in colorectal cancer.

For Control A, human dermal keratinocytes were left untreated. No irritation is expected, and therefore Control A provides a baseline (set as 0). For Control B, IL-8 is induced in human dermal keratinocytes by applying a surfactant mixture that is a combination of sodium laureth sulfate and polyquaternium-10 (set as 100%). For all other samples, the human dermal keratinocytes are co-treated with the surfactant mixture and a composition containing indicated concentration of Lipigenine™. Decreased IL-8 expression reflects an ingredient's anti-irritation activity. In order to carry out the test method, an assay kit was employed that was obtained from R&D Systems: Human CXCL8/IL-8 Duoset ELISA Kit (DY208). ELISA was performed after overnight treatment using by applying 100 μl/well of culture medium according to the manufactory instruction of the ELISA kit. The results were measured using a colorimeter, absorbance was measured at 450 nanometers (nm) within 30 minutes. Wavelength correction was set to 570 nm.

Figure 8:
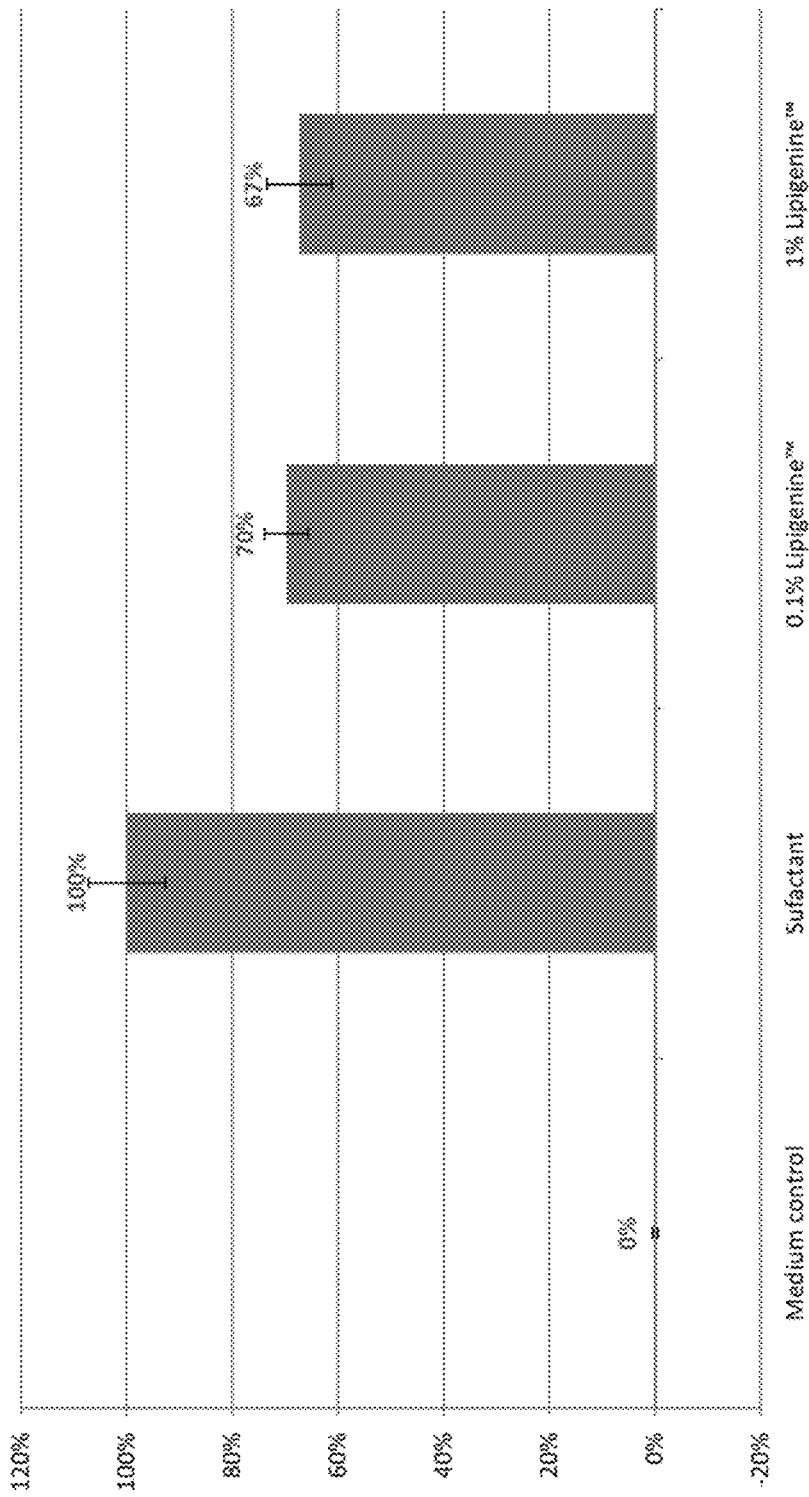
FIG. 8 graphically illustrates IL-8 concentrations after treatment with 0.1% and 1.0% Lipigenine™.
Figure 9:
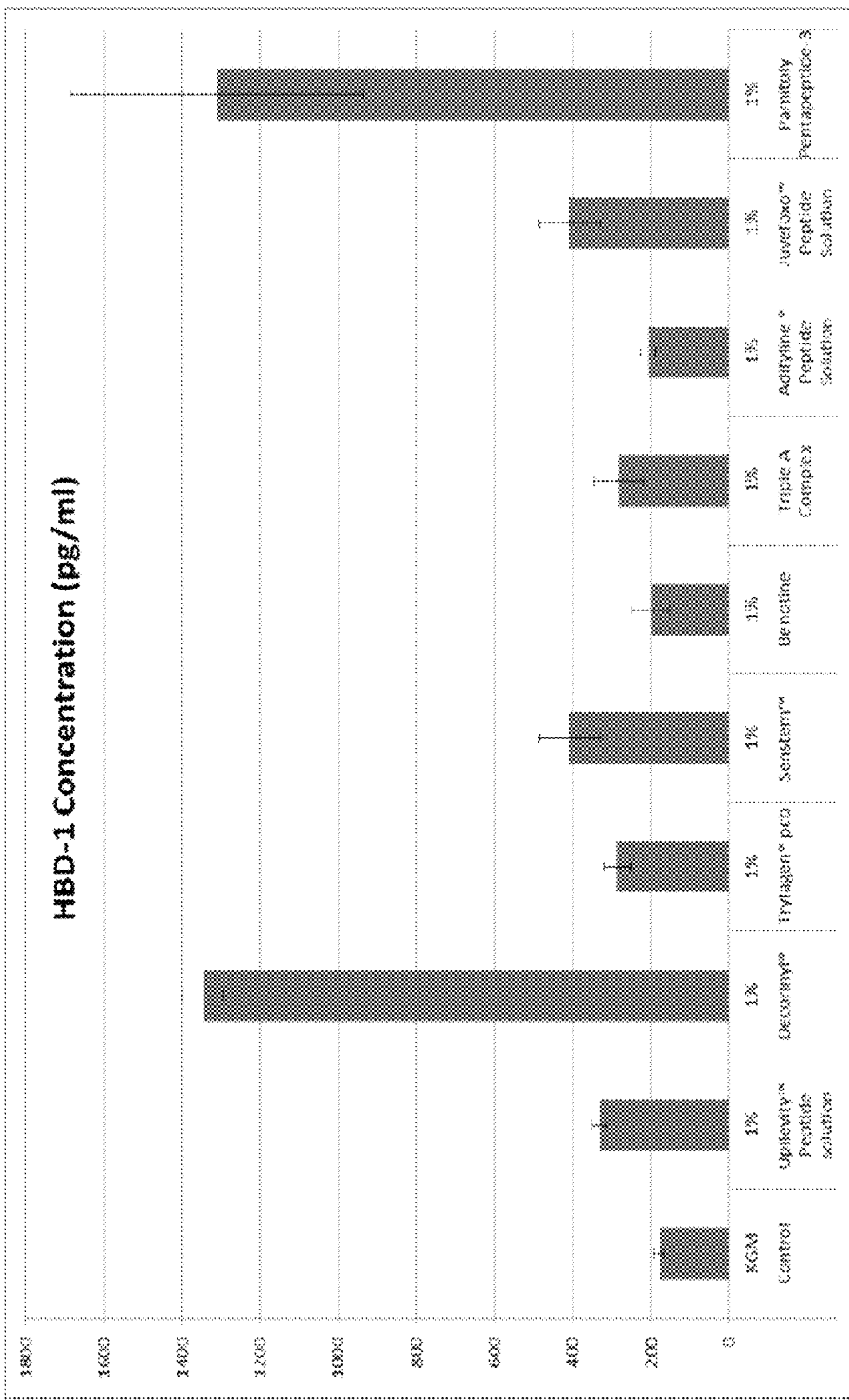
FIG. 9 graphically illustrates HBD-1 concentrations after treatment with various ingredients.
Figure 10:
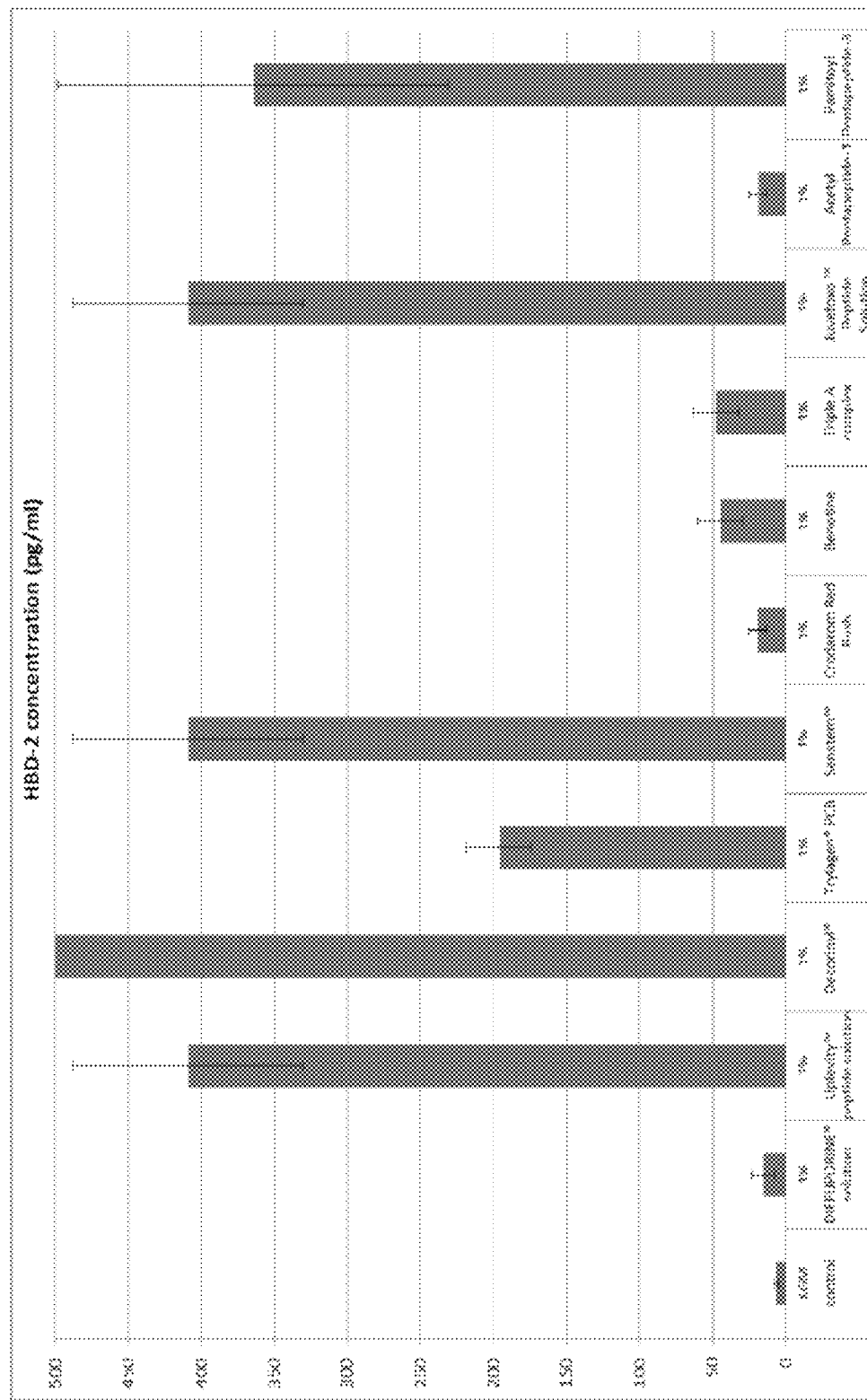
FIG. 10 graphically illustrates HBD-2 concentrations after treatment with various ingredients.
Figure 11:
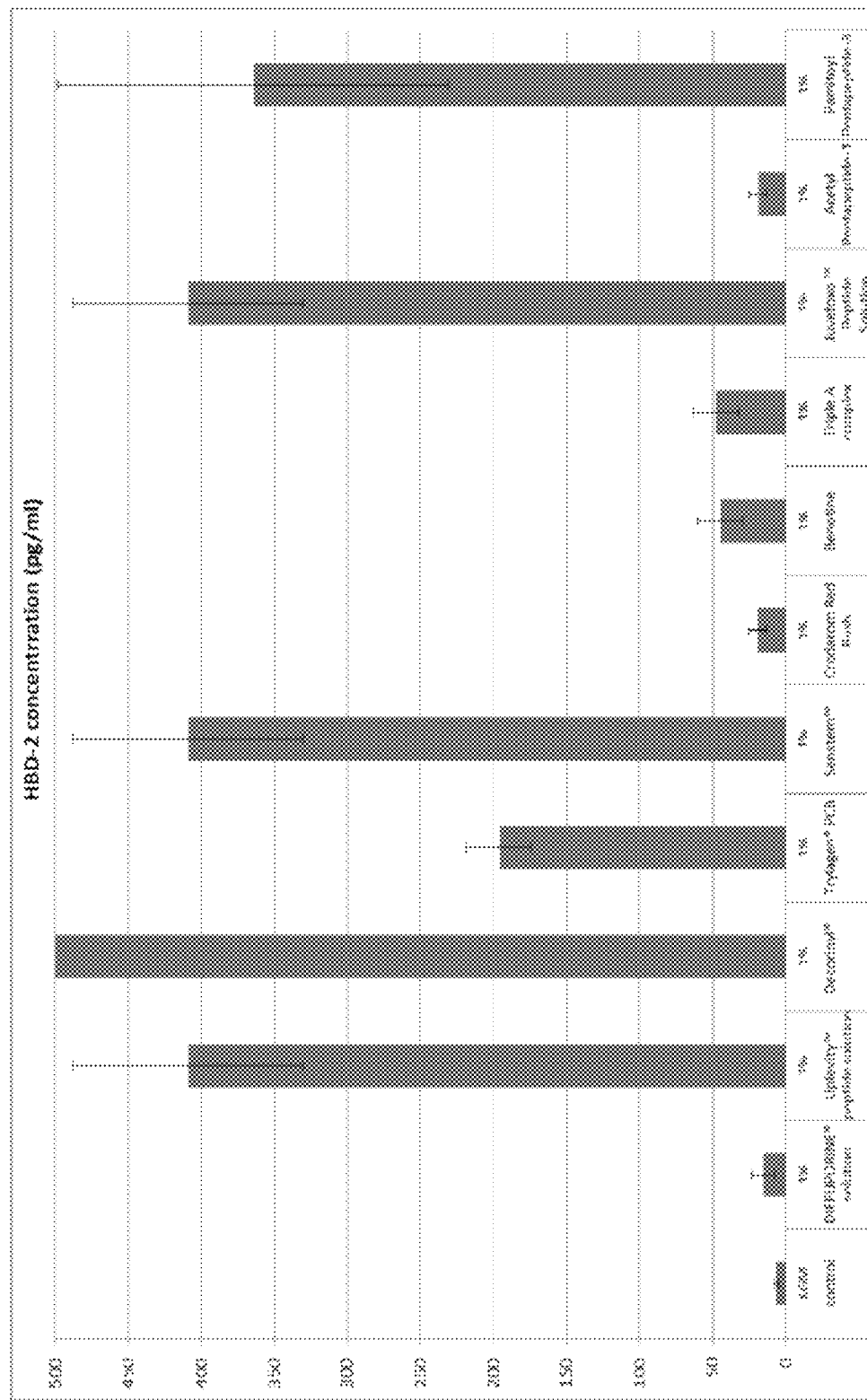
FIG. 11 graphically illustrates HBD-3 concentrations after treatment with various ingredients.

The addition of Lipigenine™ showed reduced IL-8 concentration at both 0.1% and 1% Lipigenine™ in solution as compared to a surfactant. A decrease in IL-8 concentration of 30% was observed for a 0.1% Lipigenine™ formulation while a decrease in IL-8 concentration of 33% was observed for a 1% Lipigenine™ formulation. These results are shown in FIG. 8.

EXAMPLE 9

Tape stripping tests were also performed with 5% Lipigenine™ in a soap base formulation (rinse-off) to determine the concentration of AMPs including HBD-1, HBD-2, and HBD-3 on the skin as compared to a soap base without Lipigenine™ (rinse-off). A higher concentration of Lipigenine™ was needed in this example because the formulation was being washed off of the skin instead of being left on. Seven (7) layers of tape strips were applied to the skin at two adjacent sites for both the soap base with Lipigenine™ and the soap base without Lipigenine™. The strips were applied after the two soap bases had been used to clean each skin site. After application, the first layer of tape was discarded as there was too much noise to properly analyze the strip. Thereafter, layers 2-4 were combined (the "Upper Layers") and layers 5-7 were combined (the "Lower Layers"). These tape striping experiments were run at 0 days (before application), 5 days after application, and 10 days after application to observe increases in AMP concentration over time. Each of the Upper Layers and the Lower Layers were placed in a glass vial and frozen until analysis. Increases in HBD-1 concentration of about 13 pg/mL and about 16 pg/mL were observed for the Upper Layers after 5 days and the Lower Layers after 5 days, respectfully for the soap base with Lipigenine™ as compared to a soap base without Lipigenine™. A statistically significant (95% confidence) increase in HBD-2 concentration of about 63 ng/mL was observed after 5 days in the Lower Layers for the soap base with Lipigenine™ as compared to a soap base without Lipigenine™. A statistically significant (90% confidence) increase in HBD-3 concentration of over 189 pg/mL in HBD-3 was observed after 5 days in the Lower Layers for the soap base with Lipigenine™ as compared to a soap base without Lipigenine™. These results are shown below in Table 4.

TABLE 4

| Layer/Day | 5% Lipigenine ™ in ALSO Soap Base used as a rinse-ff (Code-W) | (Soap Control) ALSO Soap Base used as a rinse-off (Code-R) | (Standard Control) Untreated Skin Control (Code-U) |
|---|---|---|---|
| | HBD-1 Concentration (pg/mL) 2-4 Upper Layers | | |
| 0 days | 0 | 0 | 0 |
| 5 days | −7.915 | −5.004 | 0.000 |
| 10 days | −2.209 | 1.696 | 0.000 |
| | 5-7 Lower Layers | | |
| 0 days | 0 | 0 | 0 |
| 5 days | 9.904 | −6.579 | 0.000 |
| 10 days | 5.223 | −1.794 | 0.000 |

TABLE 4-continued

| Layer/Day | 5% Lipigenine ™ in ALSO Soap Base used as a rinse-ff (Code-W) | (Soap Control) ALSO Soap Base used as a rinse-off (Code-R) | (Standard Control) Untreated Skin Control (Code-U) |
|---|---|---|---|
| HBD-2 Concentration (pg/mL) 2-4 Upper Layers | | | |
| 0 days | 0 | 0 | 0 |
| 5 days | −26.890 | −17.583 | 0.000 |
| 10 days | −7.192 | 10.595 | 0.000 |
| 5-7 Lower Layers | | | |
| 0 days | 0 | 0 | 0 |
| 5 days | 35.334 R | −27.588 | 0.000 |
| 10 days | 27.552 | −7.822 | 0.000 |
| HBD-3 Concentration (pg/mL) 2-4 Upper Layers | | | |
| 0 days | 0 | 0 | 0 |
| 5 days | 22.321 | −51.342 | 0.000 |
| 10 days | 59.166 | 1.666 | 0.000 |
| 5-7 Lower Layers | | | |
| 0 days | 0 | 0 | 0 |
| 5 days | 168.683 r | −21.325 | 0.000 |
| 10 days | 141.267 | 22.110 | 0.000 |

Although embodiments of the invention have been described herein, it should be appreciated that many modifications can be made without departing from the spirit and scope of the general inventive concepts. All such modifications are intended to be included within the scope of the invention, which is to be limited only by the following claims

The invention claimed is:

1. A topical cleansing composition for stimulating the production of antimicrobial peptides on the skin, said topical cleansing composition comprising:
   about 0.02 wt. % to about 5 wt.% of an active ingredient, the active ingredient comprising at least one of linseed extract, flaxseed extract, hemp seed extract, and grapefruit seed extract;
   about 3 wt. % to about 13 wt. % of one or more primary surfactants comprising sodium laureth sulfate;
   one or more foaming agents in an amount up to about 35 wt.%; and
   water, wherein the topical cleansing composition increases the concentration of antimicrobial peptides on skin, as compared to an otherwise identical topical composition without the active ingredient.

2. The topical cleansing composition of claim 1, wherein the active ingredient is a polypeptide.

3. The topical cleansing composition of claim 1, wherein the topical cleansing composition comprises about 0.05 to about 5.0 wt. % active ingredient, based on the weight of the total composition.

4. The topical cleansing composition of claim 1, wherein the topical cleansing composition comprises about 0.1 to about 1.0 wt. % active ingredient, based on the weight of the total composition.

5. The topical cleansing composition of claim 1, wherein the topical composition comprises one or more humectants, selected from the group consisting of propylene glycol, hexylene glycol, 1,4-dihydroxyhexane, 1,2,6-hexanetriol, sorbitol, butylene glycol, caprylyl glycol, propanediols, dipropylene glycol, triethylene glycol, glycerin, polyethylene glycols, ethoxydiglycol, polyethylene sorbitol, and combinations thereof.

6. The topical cleansing composition of claim 5, wherein the humectant is present in an amount up to about 20.0 wt. %, based on the weight of the total composition.

7. The topical cleansing composition of claim 1, wherein the topical composition increases the concentration of HBD-1 by at least about 10%, relative to an otherwise identical topical composition without said active ingredient.

8. The topical cleansing composition of claim 1, wherein the topical composition increases the concentration of HBD-2 by at least about 5%, relative to an otherwise identical topical composition without said active ingredient.

9. The topical cleansing composition of claim 1, wherein the topical composition increases the concentration of HBD-3 by at least about 5%, relative to an otherwise identical topical composition without said active ingredient.

10. The topical cleansing composition of claim 1, wherein the topical composition increases the concentration of LL-37 by at least about 5%, relative to an otherwise identical topical composition without said active ingredient.

11. The topical cleansing composition of claim 1, wherein the topical composition decreases the concentration of IL-8 by at least about 5%, relative to an otherwise identical topical composition without said active ingredient.

* * * * *